(12) United States Patent
Allen et al.

(10) Patent No.: US 7,985,740 B2
(45) Date of Patent: Jul. 26, 2011

(54) PURINE DERIVATIVES AS AGONISTS OF THE ADENOSINE A2A RECEPTOR

(75) Inventors: David George Allen, Stevenage (GB); Michael David Barker, Stevenage (GB); Richard Peter Charles Cousins, Stevenage (GB)

(73) Assignee: Glaxo Group Limited, Greenforo, Middlesex (GB)

( * ) Notice: Subject to any disclaimer, the term of this patent is extended or adjusted under 35 U.S.C. 154(b) by 46 days.

(21) Appl. No.: 11/995,921

(22) PCT Filed: Jul. 17, 2006

(86) PCT No.: PCT/EP2006/007078
§ 371 (c)(1),
(2), (4) Date: Jan. 16, 2008

(87) PCT Pub. No.: WO2007/009757
PCT Pub. Date: Jan. 25, 2007

(65) Prior Publication Data
US 2008/0214581 A1    Sep. 4, 2008

(30) Foreign Application Priority Data
Jul. 19, 2005    (GB) .................................. 0514809.3

(51) Int. Cl.
*A61K 31/70*    (2006.01)
*C07H 19/16*    (2006.01)

(52) U.S. Cl. .......................... 514/45; 514/46; 536/27.22

(58) Field of Classification Search .................. None
See application file for complete search history.

(56) References Cited

U.S. PATENT DOCUMENTS

| | | | |
|---|---|---|---|
| 3,796,700 A | 3/1974 | Yoshioka et al. | |
| 3,864,483 A | 2/1975 | Stein et al. | |
| 3,966,917 A | 6/1976 | Prasad et al. | |
| 3,983,104 A | 9/1976 | Vorbruggen | |
| 4,167,565 A | 9/1979 | Stein et al. | |
| 4,224,438 A | 9/1980 | Fauland et al. | |
| 4,663,313 A | 5/1987 | Bristol et al. | |
| 4,704,381 A | 11/1987 | Schaumann et al. | |
| 4,757,747 A | 7/1988 | Hamilton et al. | |
| 4,767,747 A | 8/1988 | Hamilton et al. | |
| 4,855,288 A | 8/1989 | Gadient et al. | |
| 4,962,194 A | 10/1990 | Bridges | |
| 4,968,697 A | 11/1990 | Hutchison | |
| 4,985,409 A | 1/1991 | Yamada et al. | |
| 5,023,244 A | 6/1991 | Goto et al. | |
| 5,043,325 A | 8/1991 | Olsson et al. | |
| 5,106,837 A | 4/1992 | Carson et al. | |
| 5,219,839 A | 6/1993 | Bru-Magniez et al. | |
| 5,219,840 A | 6/1993 | Gadient et al. | |
| 5,280,015 A | 1/1994 | Jacobson et al. | |
| 5,364,862 A | 11/1994 | Spada et al. | |
| 5,424,297 A | 6/1995 | Rubio et al. | |
| 5,446,139 A | 8/1995 | Seela et al. | |
| 5,459,255 A | 10/1995 | Cook et al. | |
| 5,646,128 A | 7/1997 | Firestein et al. | |
| 6,232,297 B1 * | 5/2001 | Linden et al. ................... 514/46 |
| 6,426,337 B1 | 7/2002 | Cox et al. | |
| 6,495,528 B1 | 12/2002 | Allen et al. | |
| 6,528,494 B2 | 3/2003 | Cox et al. | |
| 6,531,457 B2 * | 3/2003 | Linden et al. ................... 514/46 |
| 6,534,486 B1 | 3/2003 | Allen et al. | |
| 6,703,405 B2 | 3/2004 | Hofmeister et al. | |
| 6,710,051 B1 | 3/2004 | Trier | |
| 6,710,086 B1 | 3/2004 | Lai et al. | |
| 6,740,655 B2 | 5/2004 | Magee et al. | |
| 6,753,322 B2 | 6/2004 | Mantell et al. | |
| 6,756,392 B2 | 6/2004 | Magee | |
| 6,762,170 B1 * | 7/2004 | Chan et al. ...................... 514/45 |
| 6,803,457 B1 | 10/2004 | DeNinno et al. | |
| 6,841,549 B1 | 1/2005 | Asano et al. | |
| 6,844,362 B2 | 1/2005 | Brown et al. | |
| 6,849,629 B2 | 2/2005 | Mylari | |
| 6,852,746 B2 | 2/2005 | Silk et al. | |
| 7,214,665 B2 * | 5/2007 | Linden et al. ................... 514/46 |
| 7,226,913 B2 * | 6/2007 | Linden et al. ................... 514/46 |
| 7,378,400 B2 * | 5/2008 | Rieger et al. ................... 514/46 |
| 7,427,606 B2 * | 9/2008 | Linden et al. ................... 514/46 |
| 2004/0044211 A1 | 3/2004 | Hofmeister et al. | |
| 2004/0053953 A1 | 3/2004 | Taveras et al. | |
| 2004/0053982 A1 | 3/2004 | Press et al. | |
| 2004/0067902 A9 | 4/2004 | Bratzler et al. | |
| 2004/0067954 A1 | 4/2004 | Eggenweiler et al. | |
| 2004/0077584 A1 | 4/2004 | Mantell et al. | |
| 2004/0082578 A1 | 4/2004 | Heintzelman et al. | |
| 2004/0106572 A1 | 6/2004 | Fishman et al. | |

(Continued)

FOREIGN PATENT DOCUMENTS
BE    768925 A    6/1971

(Continued)

OTHER PUBLICATIONS

Asako et al.; "Leukocyte adherence in rat mesenteric venules: effects of adenosine and methotrexate"; Gastroenterology; 1993; vol. 104; pp. 31-37.

Baker et al.; "5'-substituted-5'-deoxy nucleosides"; Tetrahedron; 1974; vol. 30, No. 16; pp. 2939-2942.

Bedford et al.; "Nonquaternary cholinesterase reactivators, 3. 3(5)-Substituted 1,2,4-oxadiazol-5(3)-aldoximes and 1,2,4-oxadiazole-5(3)-thiocarbohydroximates as reactivators of organophosphonate-inhibited eel and human acetylcholinesterase in vitro"; J. Med. Chem.; 1986; vol. 29, No. 11; pp. 2174-2183.

Burkey et al.; "Adenosine inhibits fMLP-stimulated adherence and superoxide anion generation by human neutrophils at an early step in signal transduction"; Biochem. Biophys. Acta; 1993; vol. 1175, No. 3; pp. 312-318.

Cariello et al.; "Comparison of the computer programs DEREK and TOPKAT to predict bacterial mutagenicity"; Mutagenesis; 2002; vol. 17, No. 4; pp. 321-329.

(Continued)

*Primary Examiner* — Lawrence E Crane
(74) *Attorney, Agent, or Firm* — Robert J. Smith

(57) ABSTRACT

The invention provides novel compounds which are agonists of the adenosine 2A receptor along with pharmaceutical compositions thereof, and methods of administering such compounds.

15 Claims, No Drawings

U.S. PATENT DOCUMENTS

| | | | |
|---|---|---|---|
| 2004/0116376 A1 | 6/2004 | Elzein et al. |
| 2004/0116503 A1 | 6/2004 | Brown et al. |
| 2004/0121978 A1 | 6/2004 | Cristalli |
| 2004/0122045 A1 | 6/2004 | Xu et al. |
| 2004/0127452 A1 | 7/2004 | Van Tilburg et al. |
| 2004/0127510 A1 | 7/2004 | Heintzelman et al. |
| 2004/0132686 A1 | 7/2004 | Van Tilburg et al. |
| 2004/0138175 A1 | 7/2004 | Magde et al. |
| 2004/0142037 A1 | 7/2004 | Engelmayer et al. |
| 2004/0143014 A1 | 7/2004 | Bertrand et al. |
| 2004/0171576 A1 | 9/2004 | Yeadon et al. |
| 2004/0171798 A1 | 9/2004 | Magee et al. |
| 2004/0175382 A1 | 9/2004 | Schafer |
| 2004/0184995 A1 | 9/2004 | Katsuma et al. |
| 2004/0186142 A1 | 9/2004 | Taveras et al. |
| 2004/0198693 A1 | 10/2004 | DeNinno et al. |
| 2004/0204481 A1 | 10/2004 | Fishman |
| 2004/0224975 A1 | 11/2004 | Balley et al. |
| 2004/0229780 A1 | 11/2004 | Olivera |
| 2004/0229838 A1 | 11/2004 | Mantell et al. |
| 2004/0229904 A1 | 11/2004 | Bunnage et al. |
| 2004/0235774 A1 | 11/2004 | Bratzler et al. |
| 2004/0235833 A1 | 11/2004 | Brown et al. |
| 2004/0248928 A1 | 12/2004 | Downey et al. |
| 2004/0258740 A1 | 12/2004 | Thompson |
| 2004/0259863 A1 | 12/2004 | Eggenweiler et al. |
| 2004/0261190 A1 | 12/2004 | Eggenweiler et al. |
| 2005/0004182 A1 | 1/2005 | Brown et al. |
| 2005/0009864 A1 | 1/2005 | Hofmeister et al. |
| 2005/0014763 A1 | 1/2005 | Brown et al. |
| 2005/0020587 A1 | 1/2005 | Bailey et al. |
| 2005/0020611 A1 | 1/2005 | Barber et al. |
| 2005/0020626 A1 | 1/2005 | Mathias |
| 2005/0020639 A1 | 1/2005 | Smith et al. |
| 2005/0026952 A1 | 2/2005 | Mathias |
| 2005/0032838 A1 | 2/2005 | Bailey et al. |
| 2005/0038033 A1 | 2/2005 | Bunnage et al. |
| 2005/0043326 A1 | 2/2005 | Barber et al. |
| 2005/0059686 A1 | 3/2005 | Eggenweiler et al. |
| 2005/0085437 A1 | 4/2005 | Silk et al. |
| 2005/0085526 A1 | 4/2005 | Brown et al. |

FOREIGN PATENT DOCUMENTS

| | | |
|---|---|---|
| CA | 1077931 A1 | 5/1980 |
| CA | 1082695 A1 | 7/1980 |
| DE | 2034785 A | 1/1972 |
| DE | 2213180 A | 9/1972 |
| DE | 2317770 A | 10/1973 |
| DE | 2621470 | 12/1977 |
| EP | 0066918 A1 | 12/1982 |
| EP | 0139358 A2 | 5/1985 |
| EP | 0181128 A2 | 5/1986 |
| EP | 0181129 A2 | 5/1986 |
| EP | 0222330 A2 | 5/1987 |
| EP | 0232813 A2 | 8/1987 |
| EP | 0253962 A2 | 1/1988 |
| EP | 0277917 A2 | 8/1988 |
| EP | 0139358 A2 | 11/1988 |
| EP | 0423776 A2 | 4/1991 |
| EP | 0423777 A2 | 4/1991 |
| EP | 0496617 A1 | 7/1992 |
| EP | 0773023 A1 | 5/1997 |
| EP | 1396269 A1 | 3/2004 |
| EP | 1396270 A1 | 3/2004 |
| EP | 1400245 A1 | 3/2004 |
| EP | 1407769 A1 | 4/2004 |
| EP | 1296996 B1 | 5/2004 |
| EP | 1252157 B1 | 6/2004 |
| EP | 1460064 A1 | 9/2004 |
| EP | 1466916 A1 | 10/2004 |
| EP | 1466917 A1 | 10/2004 |
| EP | 1477167 A1 | 11/2004 |
| EP | 1373259 B1 | 12/2004 |
| EP | 1383515 B1 | 12/2004 |
| EP | 1486204 A1 | 12/2004 |
| EP | 1491540 A1 | 12/2004 |
| EP | 1491541 A1 | 12/2004 |
| EP | 1229034 B1 | 4/2005 |
| EP | 1252158 B1 | 4/2005 |
| EP | 1365776 B1 | 4/2005 |
| GB | 1386656 A | 2/1972 |
| GB | 1399670 A | 7/1975 |
| GB | 2199036 A | 6/1988 |
| GB | 2203149 A | 10/1988 |
| JP | 58167599 | 10/1983 |
| JP | 58174322 | 10/1983 |
| WO | 8600310 A1 | 1/1986 |
| WO | 8803147 A1 | 5/1988 |
| WO | 8803148 A2 | 5/1988 |
| WO | 8908658 A | 9/1989 |
| WO | 9110671 A1 | 7/1991 |
| WO | 9113082 A1 | 9/1991 |
| WO | 9203463 A | 3/1992 |
| WO | 9205177 A1 | 4/1992 |
| WO | 9314102 A1 | 7/1993 |
| WO | 9322328 A | 11/1993 |
| WO | 9402497 A1 | 2/1994 |
| WO | 9417090 A1 | 8/1994 |
| WO | 9417803 A1 | 8/1994 |
| WO | 9418215 A1 | 8/1994 |
| WO | 9502604 A1 | 1/1995 |
| WO | 9511904 A1 | 5/1995 |
| WO | 9518817 A1 | 7/1995 |
| WO | 9602543 A1 | 2/1996 |
| WO | 9602553 A2 | 2/1996 |
| WO | 9636729 A1 | 11/1996 |
| WO | 9740056 A1 | 10/1997 |
| WO | 9801426 A1 | 1/1998 |
| WO | 9801459 A1 | 1/1998 |
| WO | 9816539 A1 | 4/1998 |
| WO | 9828316 A1 | 7/1998 |
| WO | 9828319 A | 7/1998 |
| WO | WO98/28319 A1 * | 7/1998 |
| WO | 9938877 A2 | 8/1999 |
| WO | 9941267 A1 | 8/1999 |
| WO | 9967263 A1 | 12/1999 |
| WO | 9967264 A1 | 12/1999 |
| WO | 9967265 A | 12/1999 |
| WO | WO99/67265 A1 * | 12/1999 |
| WO | 0050011 A1 | 8/2000 |
| WO | 0157025 A1 | 8/2001 |
| WO | 0200200 A1 | 1/2002 |
| WO | 0200676 A1 | 1/2002 |
| WO | 02036816 A2 | 5/2002 |
| WO | 02067909 A1 | 9/2002 |
| WO | 02070532 A2 | 9/2002 |
| WO | 02072067 A2 | 9/2002 |
| WO | 02079198 A1 | 10/2002 |
| WO | 02094273 A2 | 11/2002 |
| WO | 02096462 A1 | 12/2002 |
| WO | 03014137 A1 | 2/2003 |
| WO | 03029264 A2 | 4/2003 |
| WO | 03039528 A1 | 5/2003 |
| WO | 03048180 A1 | 6/2003 |
| WO | 03061670 A1 | 7/2003 |
| WO | 03062256 A1 | 7/2003 |
| WO | 03077891 A1 | 9/2003 |
| WO | 03080604 A1 | 10/2003 |
| WO | 03080613 A | 10/2003 |
| WO | 03082787 A1 | 10/2003 |
| WO | 03088943 A1 | 10/2003 |
| WO | WO03/080613 A1 * | 10/2003 |
| WO | 03091204 A1 | 11/2003 |
| WO | 03099290 A1 | 12/2003 |
| WO | 2004022071 A1 | 3/2004 |
| WO | 2004022072 A1 | 3/2004 |
| WO | 2004022573 A2 | 3/2004 |
| WO | 2004024180 A1 | 3/2004 |
| WO | 2004028338 A2 | 4/2004 |
| WO | 2004030621 A2 | 4/2004 |
| WO | 2004032921 A1 | 4/2004 |
| WO | 2004033440 A1 | 4/2004 |
| WO | 2004038006 A2 | 5/2004 |
| WO | 2004050040 A2 | 6/2004 |
| WO | 2004052377 A1 | 6/2004 |
| WO | 2004054577 A1 | 7/2004 |

| WO | 2004062671 A2 | 7/2004 |
| WO | 2004076641 A2 | 9/2004 |
| WO | 2004078183 A1 | 9/2004 |
| WO | 2004078184 A1 | 9/2004 |
| WO | 2004079329 A2 | 9/2004 |
| WO | 2004080964 A1 | 9/2004 |
| WO | 2004084800 A2 | 10/2004 |
| WO | 2004091596 A2 | 10/2004 |
| WO | 2004100950 A1 | 11/2004 |
| WO | 2004103998 A1 | 12/2004 |
| WO | 2004108675 A1 | 12/2004 |
| WO | 2004108676 A1 | 12/2004 |
| WO | 2004110454 A1 | 12/2004 |
| WO | 2004112854 A1 | 12/2004 |
| WO | 2005009438 A1 | 2/2005 |
| WO | 2005009964 A1 | 2/2005 |
| WO | 2005009965 A1 | 2/2005 |
| WO | 2005009966 A1 | 2/2005 |
| WO | 2005009989 A1 | 2/2005 |
| WO | 2005009994 A1 | 2/2005 |
| WO | 2005009995 A1 | 2/2005 |
| WO | 2005010001 A1 | 2/2005 |
| WO | 2005012323 A2 | 2/2005 |
| WO | 2005028489 A2 | 3/2005 |
| WO | 2005116037 A | 12/2005 |
| WO | WO2005/116037 A1 * | 12/2005 |

OTHER PUBLICATIONS

Castanon et al.; "Functional Coupling of Human Adenosine Receptors to a Ligand-Dependent Reporter Gene System"; Biochem. Biophys. Res. Commun.; 1994; vol. 198, No. 2; pp. 626-631.

Cronstein et al.; "A new physiological function for adenosine: regulation of superoxide anion production"; Trans. Assoc. Am. Physicians; 1983; vol. 96; pp. 384-391.

Cronstein et al.; "Adenosine modulates the generation of superoxide anion by stimulated human neutrophils via interaction with a specific cell surface receptor"; Ann. N.Y. Acad. Sci.; 1985; vol. 451; pp. 291-301.

Cronstein et al.; "Adenosine, an endogenous anti-inflammatory agent"; J. Appl. Physiol.; 1994; vol. 76; pp. 5-13.

Cronstein et al.; "The antiinflammatory effects of methotrexate are mediated by adenosine"; Adv. Exp. Med. Biol.; 1994; vol. 370; pp. 411-416.

Cronstein et al.; "The antiinflammatory mechanism of methotrexate. Increased adenosine release at inflamed sites diminishes leukocyte accumulation in an in vivo model of inflammation"; J. Clin. Invest.; 1993; vol. 92; pp. 2675-2682.

Dianzani et al.; "Adenosine modulation of primed human neutrophils"; Eur. J. Pharmacol.; 1994; vol. 263; pp. 223-226.

Elliot et al.; "Interactions of formylmethionyl-leucyl-phenylalanine, adenosine, and phosphodiesterase inhibitors in human monocytes Effects on superoxide release, inositol phosphates and cAMP"; FEBS Letters; 1989; vol. 254, Nos. 1-2; pp. 94-98.

Flora et al.; "Antitumor Activity of Amidoximes (Hydroxyurea Analogs) in Murine Tumor Systems"; Cancer Research; 1978; vol. 38, No. 5; pp. 1291-1295.

Fozard et al.; "Adenosine receptor ligands as potential therapeutics in asthma"; Current Opinion in Investigational Drugs; 2002; vol. 3, No. 1; pp. 69-77.

Green et al.; "Purinergic regulation of bradykinin-induced plasma extravasation and adjuvant-induced arthritis in the rat"; Proc. Natl. Acad. Sci.; 1991; vol. 88, No. 10; pp. 4162-4165.

Hirschorn; "Overview of Biochemical Abnormalities and Molecular Genetics of Adenosine Deaminase Deficiency"; Pediatr. Res.; 1993; vol. 33, No. 4 (Suppl); pp. S35-S41.

Jacobson et al.; "A Novel Pharmacological Approach to Treating Cardiac Ischemia"; J. Biol. Chem.; 2000; vol. 275, No. 39; pp. 30272-30279.

Kohno et al.; "Activation of A3 adenosine receptors on human eosinophils elevates intracellular calcium"; Blood; 1996; vol. 88, No. 9; pp. 3569-3574.

Mester et al.; "Mode of Action of Some Oxidized Sugar Derivatives of Adenine on Platelet Aggregation"; Pathologie-Biologie; 1972; 20 (Suppl.); pp. 11-14.

Peachell et al.; "Inhibition by adenosine of histamine and leukotriene release from human basophils"; Biochem. Pharmacol.; 1989; vol. 38, No. 11; pp. 1717-1725.

Richter; "Effect of adenosine analogues and cAMP-raising agents on TNF-, GM-CSF—, and chemotactic peptide-induced degranulation in single adherent neutrophils"; J. Leukocyte Biol.; 1992; vol. 51, No. 3; pp. 270-275.

Rosengren et al.; "Anti-Inflammatory Effects of an Adenosine Kinase Inhibitor"; J. Immunol.; 1995; vol. 154; pp. 5444-5451.

Sanjar et al.; "TRFK5, an Antibody to Interleukin 5, Selectively Inhibits Antigen-Induced Eosinophil Accumulation in the Guinea-Pig Lung"; Am. Rev. Respir. Dis.; 1992; vol. 145; p. A40.

Schmidt et al.; "Riburonsäurederivate zur gezielten Veränderung der Ribos"; Liebigs. Ann. Chem.; 1974; vol. 1974, No. 11; pp. 1856-1863.

Skubitz et al.; "Endogenous and exogenous adenosine inhibit granulocyte aggregation without altering the associated rise in intracellular calcium concentration"; Blood; 1988; vol. 72, No. 1; pp. 29-33.

Valko et al.; "Fast gradient HPLC method to determine compounds binding to human serum albumin. Relationships with octanol/water and immobilized artificial membrane lipophilicity"; J. Pharm. Sci.; 2003; vol. 92, No. 11; pp. 2236-2248.

Van Schaick et al.; "Hemodynamic effects and histamine release elicited by the selective adenosine A3 receptor agonist 2-CI-IB-MECA in conscious rats"; Eur. J. Pharmacol.; 1996; vol. 308; pp. 311-314.

Wood; "Marker proteins for gene expression"; Current Opinion in Biotechnology; 1995; vol. 6, No. 1; pp. 50-58.

Caddell, J.M, et al., "Efficient Synthesis of an Adenosine A2a Agonist: Glycosylation of 2-Haloadenines and an N2-Alkyl-6-chloroguanine," Journal of Organic Chemistry, vol. 69(9), Apr. 30, 2004, pp. 3212-3215, XP002342820.

Jahn, W, et al., "Synthese 5'-substituierter Adenosinderivate," Chemische Berichte, vol. 98, No. 6, 1965, pp. 1705-1708.

Rosowsky, A., et al., "Synthesis of the 2-Chloro-Analogs of 3'-deoxyadenosine, 2',3'-Deoxyadenosine, and 2', 3'didehydro-2'3'-deoxyadenosine as Potential Antiviral Agents," Journal of Medicinal Chemistry, vol. 32, No, 5, May 1989, pp. 1135-1140.

Isono, K., et al., "Ascamycin and Dealanylascamycin, Nucleoside Antibiotics from Streptomyces sp." Journal of Antibiotics, vol. XXXVII, No. 6, Jun. 1984, pp. 670-672.

Hutchison et al., Journal of Medicinal Chemistry, vol. 33, No. 7, 1990, pp. 1919.-1924.

Goodman, "Chemical Syntheses and Transformations of Nucleosides," Chapter 2 in Basic Principles in Nucleic Acid Chemistry, vol. 1, P.O.P. Ts'o (ed.), Academic Press, New York, NY, 1974, pp. 94-208.

CA Listing Registry No. 210238-44-1; Aug. 20, 1998; 3,4-Furandiol,2-[6-(2.2-diphenylethyl) amino]-2-2[(2- hydrozyethyl) amino]-9H-purin-9-γl-5-(2-ethyl-2H-tetrazol-5-γ1) tetrahydro- , (2R,3R,4S,5R)-.

CA Listing Registry No. 252760-70-6; Jan. 12, 2000; 3,4-Furandiol, 2-[2-(2-aminoethyl) amino]-6-[(2,2- diphenylethyl) amino]-9H-purin-9-γ1-5-(5-ethyl-1,2,4-oxadiazol-3-γ1) tetrahydro-,(2R,3R, 4S,5R)-.

CA Listing Registry No. 252761-70-9; Jan. 12, 2000; 3,4-Furandiol, 2-(5-ethyl-3-isoxazolyl)-5-[6-(1-ethylpropyl) amino]-2-[(2-(1-piperidinyl) ethyl]amino-9H-purin-9-γl tetrahydro-,(2R,3S,4R,5R)-.

CA Listing Registry No. 210238-44-1; Aug. 20, 1998; 3,4-Furandiol, 2-[6-(2.2-diphenylethyl) amino]-2-2[(2-hydrozyethyl) amino]-9H-purin-9-γl-5-(2-ethyl-2H-tetrazol-5-γ1) tetrahydro-, (2R,3R,4S,5R)-.

CA Listing Registry No. 252760-70-6; Jan. 12, 2000; 3, 4-Furandiol, 2-[2-[92-aminoethyl0 amino]-6-[(2,2-diphenylethyl0 amino]-9H-purin-9-γl]-5-595-ethyl-1,2,3-oxadiazol-3-γl) tetrahydro-,(2R,3R, 4S,5R)-.

CA Listing Registry No. 252761-70-9; Jan. 12, 2000; 3,4-Furandiol, 2-(5-ethyl-3-isoxazolyl0-5-[6-(1-ethylpropyl) amino]-2-[[2-(1-piperidinyl) ethyl]-9H-purin-9-γl]tetrahydro-, (2R,3S,4R,5R)-.

* cited by examiner

PURINE DERIVATIVES AS AGONISTS OF THE ADENOSINE A2A RECEPTOR

CROSS-REFERENCE TO RELATED APPLICATIONS

This application is filed pursuant to 35 USC 371 as a United States National Phase Application of International Patent Application Serial No. PCT/EP2006/007078 filed on 17 Jul. 2006, which claims priority from GB 0514809.3 filed on 19 Jul. 2005 in the United Kingdom.

This invention relates to new chemical compounds, processes for their preparation, pharmaceutical formulations containing them and to their use in therapy.

Inflammation is a primary response to tissue injury or microbial invasion and is characterised by leukocyte adhesion to the endothelium, diapedesis and activation within the tissue. Leukocyte activation can result in the generation of toxic oxygen species (such as superoxide anion), and the release of granule products (such as peroxidases and proteases). Circulating leukocytes include neutrophils, eosinophils, basophils, monocytes and lymphocytes. Different forms of inflammation involve different types of infiltrating leukocytes, the particular profile being regulated by the profile of adhesion molecule, cytokine and chemotactic factor expression within the tissue.

The primary function of leukocytes is to defend the host from invading organisms such as bacteria and parasites. Once a tissue is injured or infected a series of events occurs which causes the local recruitment of leukocytes from the circulation into the affected tissue. Leukocyte recruitment is controlled to allow for the orderly destruction and phagocytosis of foreign or dead cells, followed by tissue repair and resolution of the inflammatory infiltrate. However, in chronic inflammatory states, recruitment is often inappropriate, resolution is not adequately controlled and the inflammatory reaction causes tissue destruction.

There is evidence from both in vitro and in vivo studies to suggest that compounds active at the adenosine $A_{2A}$ receptor will have anti-inflammatory actions. The area has been reviewed by Cronstein (Cronstein B N, (1994), J. Appl. Physiol. 76, pp 5-13) and Jacobson (Jacobson K A & Gao Z-A (2006), Nature Reviews Drug Discovery, 5, pp 247-264). Studies on isolated neutrophils show an $A_2$ receptor-mediated inhibition of superoxide generation, degranulation, aggregation and adherence (Cronstein B N, Kramer S B, Weissmann G, Hirschhorn R, (1983), Trans. Assoc. Am. Physicians 96, pp 384-391; Cronstein B N, Kramer S B, Rosenstein E D, Weissmann G, Hirschhorn R, (1985), Ann N.Y. Acad. Sci. 451, pp 291-301; Burkey T H, Webster R O, (1993), Biochem. Biophys. Acta 1175, pp 312-318; Richter J, (1992), J. Leukocyte Biol. 51, pp 270-275; Skubitz K M, Wickman N R, Hammerschmidt D E, (1988), Blood 72, pp 29-33). When agents selective for the $A_{2A}$ receptor over the $A_{2B}$ receptor (e.g. CGS21680) have been used, the profile of inhibition appears consistent with an action on the $A_{2A}$ receptor subtype (Dianzani C, Brunelleschi S, Viano I, Fantozzi R, (1994), Eur. J. Pharmacol. 263, pp 223-226). Adenosine agonists may also down-regulate other classes of leucocytes (Elliot K R F, Leonard E J, (1989), FEBS Letters 254, pp 94-98; Peachell P T, Lichtenstein L M, Schleimer R P, (1989), Biochem. Pharmacol. 38, pp 1717-1725). Studies on whole animals have shown the anti-inflammatory effects of methotrexate to be mediated through adenosine and $A_2$ receptor activation (Asako H, Wolf R E, Granger D N, (1993), Gastroenterology 104, pp 31-37; Cronstein B N, Naime D, Ostad E, (1993), J. Clin. Invest. 92, pp 2675-2682; Cronstein B N, Naime D, Ostad E, (1994), Adv. Exp. Med. Biol. 370, pp 411-416). The selective A2A agonist, CGS-21680 has shown anti-inflammatory activity in rats in pulmonary inflammation induced by allergen challenge and is blocked by pre-treatment with selective A2A receptor antagonist ZM241385 (Fozard, John R.; Ellis, Karen M.; Villela Dantas, Maria F.; Tigani, Bruno; Mazzoni, Lazzaro, European Journal of Pharmacology (2002), 438(3), 183-188). Adenosine itself, and compounds that raise circulating levels of adenosine also show anti-inflammatory effects in vivo (Green P G, Basbaum A I, Helms C, Levine J D, (1991), Proc. Natl. Acad Sci. 88, pp 4162-4165; Rosengren S, Bong G W, Firestein G S, (1995), J. Immunol. 154, pp 5444-5451). In addition raised levels of circulating adenosine in man (as a result of adenosine deaminase deficiency) results in immunosuppression (Hirschorn R, (1993), Pediatr. Res. 33, pp S35-41) and the crucial role A2A receptors play in limiting and terminating inflammation has been reported by Ohta (Ohta, A & Sitkovsky, M, Nature, (2001), 414, pp 916-920; Sitkovsky, M V & Ohta, A, Trends in Immunology, (2005), 26, pp 299-304).

We have now found novel compounds which inhibit leukocyte recruitment and activation and which are potent agonists of the adenosine $2_A$ (hereinafter $A_{2A}$) receptor. The compounds are therefore of potential therapeutic benefit in providing protection from leukocyte-induced tissue damage in diseases where leukocytes are implicated at the site of inflammation. The compounds of the invention may also represent a safer alternative to corticosteroids in the treatment of inflammatory diseases, whose uses may be limited by their side-effect profiles.

Further, the compounds of the invention may show an improved profile over known $A_{2A}$-selective agonists in that they may possess one or more of the following properties:

(I) approximately 100 fold more selective for $A_{2A}$ over the human $A_3$ receptor;
(II) approximately 100 fold more selective for $A_{2A}$ over the human $A_{2B}$ receptor;
(III) approximately 100 fold more selective for $A_{2A}$ over the human $A_1$ receptor;
(IV) greater than approximately 90% binding to human serum albumin; and
(V) less pronounced cardiovascular effects, in particular reduced tachycardia.

This profile can be considered of benefit as $A_3$ receptors are also found on leucocytes (e.g. eosinophils) and other inflammatory cells (e.g. mast cells) and activation of these receptors may have pro-inflammatory effects (Kohno Y, Xiao-duo J, Mawhorter S D, Koshiba M, Jacobson K A, (1996), Blood 88 pp 3569-3574; 1996; Van Schaick E A, Jacobson K A, Kim H O, Ijzerman A P, Danhof M, (1996), Eur. J. Pharmacol. 308 pp 311-314). It is even considered that the bronchoconstrictor effects of adenosine in asthmatics may be mediated via the adenosine $A_3$ receptor (Kohno Y, Xiao-duo J, Mawhorter S D, Koshiba M, Jacobson K A, (1996), Blood 88 pp 3569-3574). $A_{2B}$ receptors are also found on mast cells and may thus be implicated in mast cell activation. $A_1$ receptors have a wide tissue distribution and can be found on inter alia heart, adipocytes, respiratory smooth muscle, neutrophils, kidney, hippocampus and cortex. $A_1$ receptor activation may thus cause decreased lipolysis, diuresis and CNS activation (Fozard J R, McCarthy C, (2002), Current Opinion in Investigational Drugs 3 pp 69-77). A compound that exhibits greater than approximately 90% binding to human serum albumin may be expected to have a reduced free fraction in whole blood.

Thus according to the invention we provide compounds of formula (I):

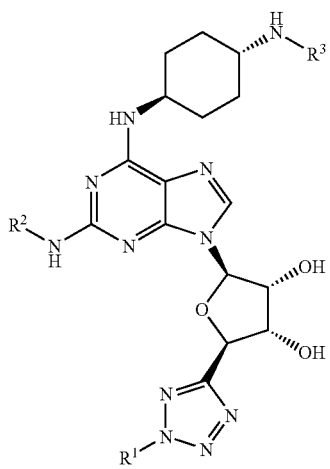
(I)

wherein:

$R^1$ represents methyl or ethyl;

$R^2$ represents a group selected from the list consisting of:

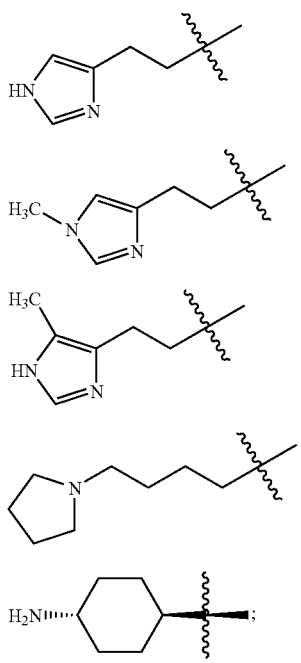

(i)

(ii)

(iii)

(iv)

(v)

$R^3$ represents a group selected from the list consisting of:

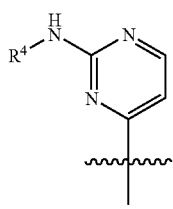
(a)

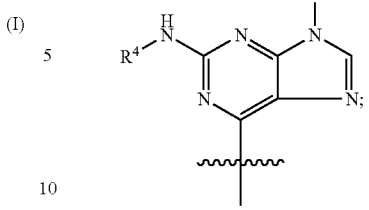
(b)

wherein $R^4$ represents a group selected from the list consisting of:

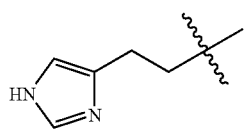
(i)

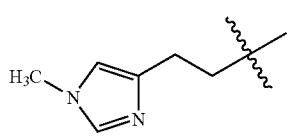
(ii)

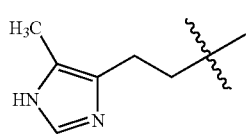
(iii)

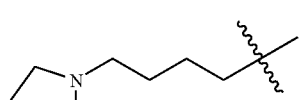
(iv)

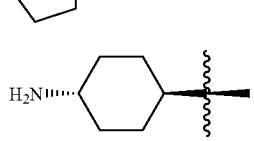
(v)

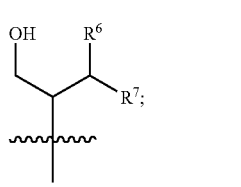
(vi)

$R^5$ represents hydrogen, $C_{1-4}$alkyl, $C_{1-4}$alkylaryl, $C_{1-4}$alkylheteroaryl or $C_{1-4}$hydroxyalkyl;

$R^6$ and $R^7$ independently represent hydrogen, methyl or phenyl;

and salts and solvates thereof.

By the term $C_{1-4}$alkyl as used herein is meant an alkyl function having between one to four carbon atoms in total, which may optionally be branched. Exemplary $C_{1-4}$alkyl groups include methyl, ethyl, propyl(n-propyl and iso-propyl) and butyl(n-butyl, sec-butyl and tert-butyl).

By the term $C_{1-4}$alkylaryl is meant a $C_{1-4}$alkyl function as described above, which is substituted by an aryl group. By the term aryl is meant a phenyl or naphthyl group which may optionally be substituted. An exemplary aryl group is phenyl. Exemplary $C_{1-4}$alkylaryl groups include benzyl.

By the term $C_{1-4}$alkylheteroaryl is meant a $C_{1-4}$alkyl function as described above, which is substituted by a heteroaryl group. By the term heteroaryl is meant a 5 or 6 membered aromatic group containing heteroatoms e.g. 1-4 heteroatoms selected from nitrogen, oxygen and sulphur. Exemplary heteroaryl groups include 5 membered rings (e.g. pyrrole, furan, thiophene) and 6 membered rings (e.g. pyridine, pyrimidine and pyrazine).

By the term $C_{1-4}$hydroxyalkyl is meant a $C_{1-4}$alkyl function as described above which is substituted with one or more (e.g. 1) hydroxyl groups.

Alkyl groups, whether as a group or part of a group, may optionally be substituted by one or more (e.g. one) fluorine atoms. Exemplary fluorine substituted alkyl groups include fluoromethyl and trifluoromethyl.

Aryl and heteroaryl groups may optionally be substituted, for example by one or more groups selected from amino, cyano, halo (e.g. fluorine or chlorine), nitro, thio and methoxy (optionally substituted by halo, e.g. trifluoromethoxy).

$R^1$ may for example represent ethyl.

$R^2$ may for example represent group (i), (ii), (iii) or (iv), e.g. group (iv). In one embodiment of the invention $R^2$ represents group (ii) or (iv). In another embodiment of the invention $R^2$ represents group (ii). In a further embodiment of the invention $R^2$ represents group (iv).

In one embodiment of the invention $R^3$ represents group (a). In a second embodiment of the invention $R^3$ represents group (b).

$R^4$ may for example represent group (i), (ii), (iii), (iv) or (v) e.g. group (i), (ii), (iii) or (iv), e.g. group (iv). In one embodiment of the invention $R^4$ represents group (ii) or (iv). In another embodiment of the invention $R^4$ represents group (ii). In a further embodiment of the invention $R^4$ represents group (iv).

$R^5$ may, for example, represent hydrogen.

$R^6$ may, for example, represent phenyl.

$R^7$ may, for example, represent hydrogen.

An example of the group (vi) moiety is the following group, derived from L-phenylaninol:

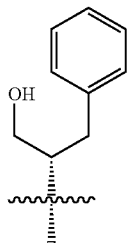

In one embodiment of the invention $R^2$ and $R^4$ are the same. In a second embodiment of the invention $R^2$ and $R^4$ are not the same.

In one embodiment of the invention the compound of formula (I) is:

(2R,3S,4R,5R)-2-(2-ethyl-2H-tetrazol-5-yl)-5-[2-{[2-(1H-imidazol-4-yl)ethyl]amino}-6-({trans-4-[(2-{[2-(1H-imidazol-4-yl)ethyl]amino}-1H-purin-6-yl)amino] cyclohexyl}amino)-9H-purin-9-yl]tetrahydro-3,4-furandiol;

(2R,3S,4R,5R)-2-(2-ethyl-2H-tetrazol-5-yl)-5-[2-{[2-(1-methyl-1H-imidazol-4-yl)ethyl]amino}-6-({trans-4-[(2-{[2-(1-methyl-1H-imidazol-4-yl)ethyl]amino}-1H-purin-6-yl)amino]cyclohexyl}amino)-9H-purin-9-yl]tetrahydro-3,4-furandiol;

(2R,3S,4R,5R)-2-(2-ethyl-2H-tetrazol-5-yl)-5-[2-{[2-(5-methyl-1H-imidazol-4-yl)ethyl]amino}-6-({trans-4-[(2-{[2-(5-methyl-1H-imidazol-4-yl)ethyl]amino}-1H-purin-6-yl)amino]cyclohexyl}amino)-9H-purin-9-yl]tetrahydro-3,4-furandiol;

(2R,3S,4R,5R)-2-(2-ethyl-2H-tetrazol-5-yl)-5-[2-{[4-(1-pyrrolidinyl)butyl]amino}-6-({trans-4-[(2-{[4-(1-pyrrolidinyl)butyl]amino}-1H-purin-6-yl)amino]cyclohexyl}amino)-9H-purin-9-yl]tetrahydro-3,4-furandiol;

(2R,3R,4S,5R)-2-(2-[(trans-4-aminocyclohexyl)amino]-6-{[trans-4-({2-[(trans-4-aminocyclohexyl)amino]-9H-purin-6-yl}amino)cyclohexyl]amino}-9H-purin-9-yl)-5-(2-ethyl-2H-tetrazol-5-yl)tetrahydro-3,4-furandiol;

(2R,3S,4R,5R)-2-(2-ethyl-2H-tetrazol-5-yl)-5-[2-{[2-(1H-imidazol-4-yl)ethyl]amino}-6-({trans-4-[(2-{[2-(1H-imidazol-4-yl)ethyl]amino}-4-pyrimidinyl)amino] cyclohexyl}amino)-9H-purin-9-yl]tetrahydro-3,4-furandiol;

(2R,3S,4R,5R)-2-(2-ethyl-2H-tetrazol-5-yl)-5-[2-{[2-(1-methyl-1H-imidazol-4-yl)ethyl]amino}-6-({trans-4-[(2-{[2-(1-methyl-1H-imidazol-4-yl)ethyl]amino}-4-pyrimidinyl)amino]cyclohexyl}amino)-9H-purin-9-yl]tetrahydro-3,4-furandiol;

(2R,3S,4R,5R)-2-(2-ethyl-2H-tetrazol-5-yl)-5-[2-{[2-(5-methyl-1H-imidazol-4-yl)ethyl]amino}-6-({trans-4-[(2-{[2-(5-methyl-1H-imidazol-4-yl)ethyl]amino}-4-pyrimidinyl)amino]cyclohexyl}amino)-9H-purin-9-yl]tetrahydro-3,4-furandiol;

(2R,3S,4R,5R)-2-(2-ethyl-2H-tetrazol-5-yl)-5-[2-{[4-(1-pyrrolidinyl)butyl]amino}-6-({trans-4-[(2-{[4-(1-pyrrolidinyl)butyl]amino}-4-pyrimidinyl)amino] cyclohexyl}amino)-9H-purin-9-yl]tetrahydro-3,4-furandiol;

(2R,3R,4S,5R)-2-(2-[(trans-4-aminocyclohexyl)amino]-6-{[trans-4-({2-[(trans-4-aminocyclohexyl)amino]-4-pyrimidinyl}amino)cyclohexyl]amino}-9H-purin-9-yl)-5-(2-ethyl-2H-tetrazol-5-yl)tetrahydro-3,4-furandiol;

or a salt or solvate of any one thereof.

In a further embodiment of the invention the compound of formula (I) is:

(2R,3S,4R,5R)-2-(2-ethyl-2H-tetrazol-5-yl)-5-[2-{[2-(1-methyl-1H-imidazol-4-yl)ethyl]amino}-6-({trans-4-[(2-{[2-(1-methyl-1H-imidazol-4-yl)ethyl]amino}-1H-purin-6-yl)amino]cyclohexyl}amino)-9H-purin-9-yl]tetrahydro-3,4-furandiol;

(2R,3S,4R,5R)-2-(2-ethyl-2H-tetrazol-5-yl)-5-[2-{[4-(1-pyrrolidinyl)butyl]amino}-6-({trans-4-[(2-{[4-(1-pyrrolidinyl)butyl]amino}-1H-purin-6-yl)amino] cyclohexyl}amino)-9H-purin-9-yl]tetrahydro-3,4-furandiol;

(2R,3S,4R,5R)-2-(2-ethyl-2H-tetrazol-5-yl)-5-[2-{[2-(1-methyl-1H-imidazol-4-yl)ethyl]amino}-6-({trans-4-[(2-{[2-(1-methyl-1H-imidazol-4-yl)ethyl]amino}-4-pyrimidinyl)amino]cyclohexyl}amino)-9H-purin-9-yl]tetrahydro-3,4-furandiol;

or a salt or solvate of any one thereof.

Compounds of formula (I) require absolute stereochemistry about the tetrahydrofuran ring such that the stereochemistry about each stereocentre in the tetrahydrofuran ring is as follows:

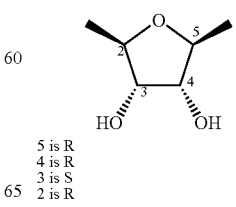

5 is R
4 is R
3 is S
2 is R

The stereochemistry about the cyclohexyl ring in the conserved core and the substituent groups where $R^2$ represents (v) or $R^4$ represents (v) are defined in relative terms. Within this requirement the invention encompasses all stereoisomers of the compounds of formula (I) (e.g. enantiomers or diastereoisomers) whether as individual stereoisomers isolated such as to be substantially free of the other stereoisomer (i.e. pure) or as mixtures thereof. An individual stereoisomer isolated such as to be substantially free of the other stereoisomer (i.e. pure) will be isolated such that less than about 10%, for example less than about 1% or less than about 0.1% of the other stereoisomer is present.

Salts of the compounds of the present invention are also encompassed within the scope of the invention. Because of their potential use in medicine, the salts of the compounds of formula (I) are preferably pharmaceutically acceptable salts. Suitable pharmaceutically acceptable salts can include acid addition salts. A pharmaceutically acceptable acid addition salt can be formed by reaction of a compound of formula (I) with a suitable inorganic or organic acid (such as hydrobromic, hydrochloric, formic, sulfuric, nitric, phosphoric, succinic, maleic, acetic, fumaric, citric, tartaric, benzoic, xinafoate, p-toluenesulfonic, methanesulfonic or naphthalenesulfonic acid), optionally in a suitable solvent such as an organic solvent, to give the salt which may be isolated for example by crystallisation and filtration. Thus, a pharmaceutically acceptable acid addition salt of a compound of formula (I) can be for example a hydrobromide, hydrochloride, formate, sulfate, nitrate, phosphate, succinate, maleate, acetate, fumarate, citrate, tartrate, benzoate, p-toluenesulfonate, methanesulfonate or naphthalenesulfonate salt. Other non-pharmaceutically acceptable salts, e.g. oxalates or trifluoroacetates, may be used, for example in the isolation of compounds of the invention, and are included within the scope of this invention. The invention includes within its scope all possible stoichiometric and non-stoichiometric forms of the salts of the compounds of formula (I).

Also included within the scope of the invention are all solvates, for example hydrates, and complexes of compounds and salts of the invention.

Compounds of formula (I), or a protected derivative thereof, may be prepared by the reaction of a compound of formula (IIA) or (IIB), or a protected derivative thereof:

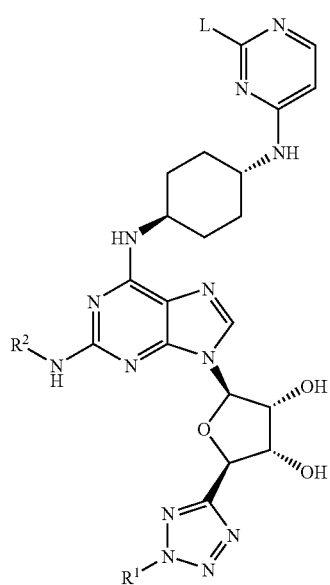

(IIA)

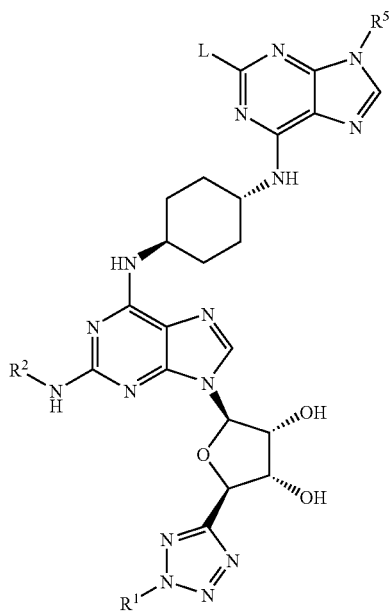

(IIB)

wherein the groups $R^1$, $R^2$ and $R^5$ are as defined above for compounds of formula (I) and L represents a leaving group; by reaction with an amine of formula (III), or a protected derivative thereof:

$$R^4-NH_2 \quad \text{(III)}$$

wherein $R^4$ is as defined above for compounds of formula (I).

L suitably represents halogen, for example bromine or chlorine, in particular chlorine. The reaction will generally involve heating the reagents to an elevated temperature of 50° C. to 150° C., such as 100° C. to 130° C., particularly about 120° C. to 130° C., in the presence of an inert solvent such as DMSO and a base, such as an amine base (e.g. diisopropylethylamine).

When $R^5$ represents hydrogen, the nitrogen to which it is attached (i.e. the 9 position of the purine ring) may suitably be protected, for example as the tetrahydropyran-2-yl derivative. Following the reaction described above for the formation of a protected derivative of a compound of formula (I), the nitrogen may then be deprotected. Suitable conditions for deprotection will depend upon the chosen protecting group, for example, where the protecting group is tetrahydropyran-2-yl suitable deprotection conditions include treatment with formic acid in methanol/water.

Compounds of formula (IIA) or (IIB), or a protected derivative thereof may be prepared by the reaction of a compound of formula (IV), or a protected derivative thereof:

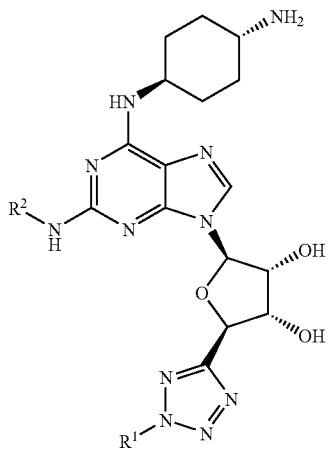

(IV)

wherein the groups R¹ and R² are as defined above for compounds of formula (I);
with a compound of formula (VA) or (VB), or a protected derivative thereof:

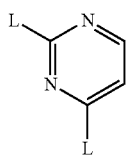

(VA)

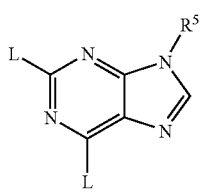

(VB)

wherein R⁵ is as defined above for compounds of formula (I) and L represents a leaving group.

L suitably represents halogen, for example bromine or chlorine, in particular chlorine. The reaction will generally be performed in the presence of a base, such as an amine base (e.g. diisopropylethylamine), in a suitable solvent, such as an alcohol (e.g. isopropanol), at an elevated temperature (e.g. 50° C. to 70° C.).

As noted above, when R⁵ represents hydrogen, the nitrogen to which it is attached (i.e. the 9 position of the purine ring) may suitably be protected, for example as the tetrahydropyran-2-yl derivative. Following the reaction described above for the formation of a protected derivative of a compound of formula (IIB), the nitrogen may then be deprotected. Suitable conditions for deprotection will depend upon the chosen protecting group, for example, where the protecting group is tetrahydropyran-2-yl suitable deprotection conditions include treatment with formic acid in methanol/water.

Compounds of formula (IV), or a protected derivative thereof, may be prepared by the reaction of a compound of formula (VI), or a protected derivative thereof:

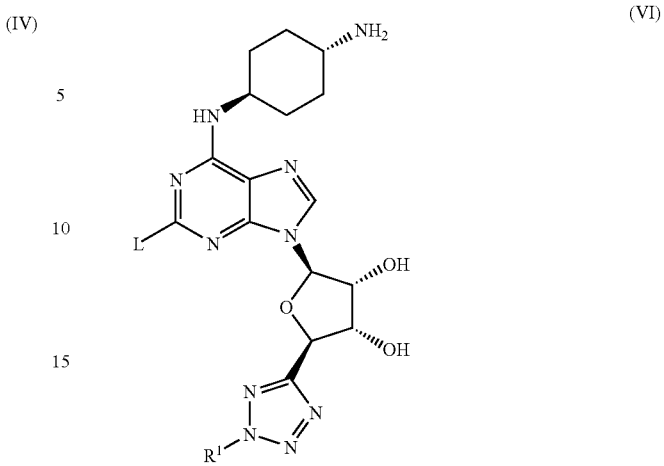

(VI)

wherein R¹ is as defined above for compounds of formula (I) and L represents a leaving group;
with an amine of formula (VII), or a protected derivative thereof:

R²—NH₂     (VII)

wherein R² is as defined above for compounds of formula (I).

L suitably represents halogen, for example bromine or chlorine, in particular chlorine. The reaction will generally involve heating the reagents to an elevated temperature of 50° C. to 150° C., such as 100° C. to 130° C., particularly about 120° C. to 130° C., in the presence of an inert solvent such as DMSO and a base, such as an amine base (e.g. diisopropylethylamine).

Suitably the primary amine group attached to the cyclohexyl ring in compounds of formula (VI) is protected, for example as the dimethylethyloxycarbonyl (Boc) derivative. Following the reaction to yield a protected derivative of a compound of formula (IV) the amine protecting group may be removed, for example, where the protecting group represents dimethylethyloxycarbonyl this may be removed, for example, by treatment with trifluoroacetic acid in dichloromethane.

When R² represents a group of formula (v), the amine function of R² may suitably be protected by a different protecting group employed to that employed to protect the amine function of the compound of formula (VI). For example the former may be protected using CbZ (which may subsequently be removed by catalytic hydrogenation) and the latter may be protected using Boc.

Compounds of formula (VI), or protected derivatives thereof, may be prepared by the reaction of a compound of formula (VIII), or a protected derivative thereof:

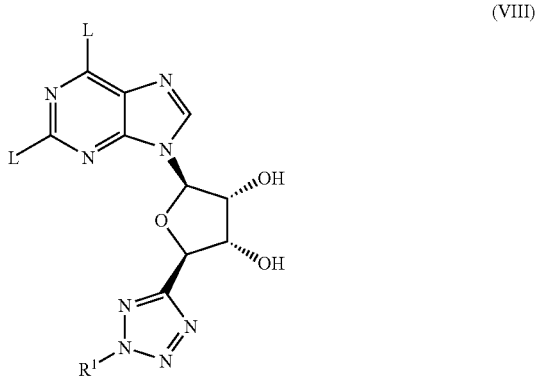

(VIII)

wherein R¹ is as defined above for compounds of formula (I) and L represents a leaving group;

with the compound of formula (IX), or a protected derivative thereof:

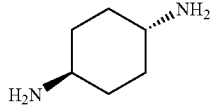
(IX)

L suitably represents halogen, for example bromine or chlorine, in particular chlorine. The reaction will typically be performed in the presence of a base, such as an amine base (e.g. diisopropylethylamine), in a suitable solvent, such as an alcohol (e.g. isopropanol), at an elevated temperature (e.g. 50° C. to 70° C.).

Compounds of formula (IX) will typically be utilised in the form in which one primary amine group is protected, for example as the dimethylethyloxycarbonyl derivative.

Compounds of formula (VIII) wherein L represents chlorine, $R^1$ represents ethyl and the hydroxyl functions are protected with acetyl groups are disclosed in WO98/28319 (referred to as Intermediate 7 therein). Other compounds of formula (VIII) may be prepared by analogous means. Briefly, a compound of formula (VIII) may be prepared by reacting a compound of formula (X), or a protected derivative thereof:

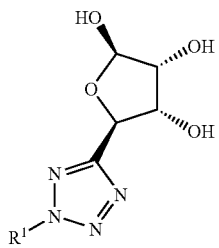
(X)

wherein $R^1$ is as defined above for compounds of formula (I); with a compound such as 2,6-dichloropurine in a suitable solvent (e.g. acetonitrile), under inert conditions and in the presence of a Lewis acid (such as trimethylsilyl triflate) and optionally with a catalyst (e.g. 1,8-diazabicyclo[5.4.0]undec-7-ene).

Compounds of formula (III), (VII), (IX) and (X) are known per se or may be prepared by known methods.

Compounds of formula (VA), for example 2,4-dichloropyrimidine, are available commercially or may be prepared by known methods.

The compound of formula (VB) wherein L represent chlorine and which is protected by a tetrahydropyran-2-yl group (i.e. 2,6-dichloro-9-(tetrahydro-2H-pyran-2-yl)-9H-purine) and a method for its synthesis are disclosed in WO2003/080604A1 (referred to as Intermediate 11 therein). Other compounds of formula (VB) may be prepared by analogous means.

In a second process, compounds of formula (I), or a protected derivative thereof, may be prepared by reacting a compound of formula (IV) as described above, or a protected derivative thereof:

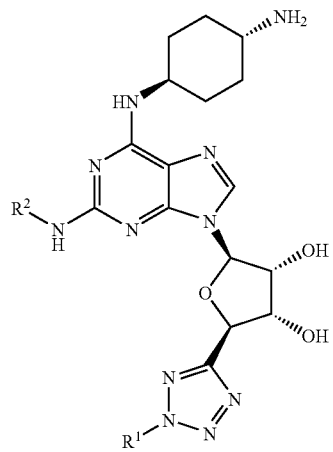
(IV)

with a compound of formula (XIA) or (XIB), or a protected derivative thereof:

(XIA)

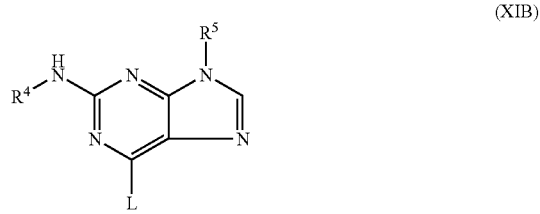
(XIB)

wherein the groups $R^4$ and $R^5$ are as defined above for compounds of formula (I) and L is a leaving group.

L suitably represents halogen, for example bromine or chlorine, in particular chlorine. Said reaction will generally involve heating the reagents to a temperature of 50° C. to 150° C., in the presence of an inert solvent such as ethanol, propan-2-ol or DMSO and a base, such as an amine base (e.g. diisopropylethylamine).

In compounds of formula (XIB) when $R^5$ represents H the nitrogen to which it is attached (i.e. the 9-position of the purine ring) may optionally be protected by a tetrahydropyran-2-yl (THP) moiety. The THP group may subsequently be removed following the reaction with a compound of formula (IV). Suitable deprotection conditions include treatment with formic acid in methanol/water.

Compounds of formula (XIA) may be prepared according to Manley P J et al. (2003) Bioorganic Med. Chem. Lett., 13 pp 1673-1677. Briefly, a compound of formula (XII), or a protected derivative thereof:

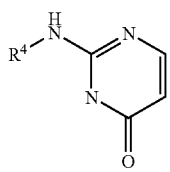

(XII)

wherein $R^4$ is as defined above for compounds of formula (I); may be reacted with $POCl_3$ under reflux.

Compounds of formula (XII) may be prepared by the reacting 2-(methylthio)-pyrimidin-4(3H)-one (commercially available) with an amine of formula (III) as described above, or a protected derivative thereof:

wherein $R^4$ is as defined above for compounds of formula (I).

The reaction is typically performed in diglyme at a temperature of approximately 170° C.

Compounds of formula (XIB) wherein $R^5$ represents H may be prepared by means described in Wright G E et al. (1987) J. Med. Chem., 30 pp 109-116. Briefly, a compound of formula (XII):

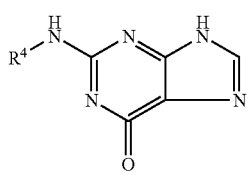

(XIII)

wherein $R^4$ is as defined above for compounds of formula (I); may be reacted with $POCl_3$ in the presence of N,N-dimethylaniline under reflux.

Compounds of formula (XIII) may be prepared by the reaction of a compound such as 2-bromohypoxanthine, which is commercially available:

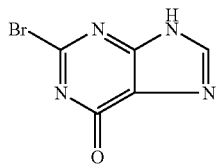

with an amine of formula (III) as described above, or a protected derivative thereof:

wherein $R^4$ is as defined above for compounds of formula (I); under reflux in a mixture of water and 2-methoxyethanol. Further details of this reaction may be obtained by reference to WO99/38877.

Compounds of formula (XIB) wherein $R^5$ does not represent H, may be prepared by the alkylation of compounds of formula (XIB) wherein $R^5$ represents H. Alkylation may be performed using an alkylating agent such as $R^5$—I, in the presence of a base (e.g. potassium carbonate) and a suitable solvent (e.g. DMF), for example see Langli, G et al. (1996) Tetrahedron, 52 pp 5625-5638. Alternatively, alkylation may be performed using an alcohol $R^5$—OH in the presence of diethylazodicarboxylate and triphenylphosphine in THF (see Maruyama, T et al. (2000) Nucleosides, Nucleotides and Nucleic Acids, 19 pp 1193-1203).

In a third process, compounds of formula (I) wherein $R^2$ and $R^4$ are the same, or a protected derivative thereof, may be prepared by reacting a compound of formula (XIVA) or (XIVB), or a protected derivative thereof:

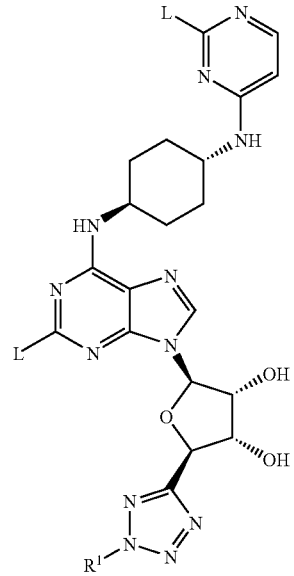

(XIVA)

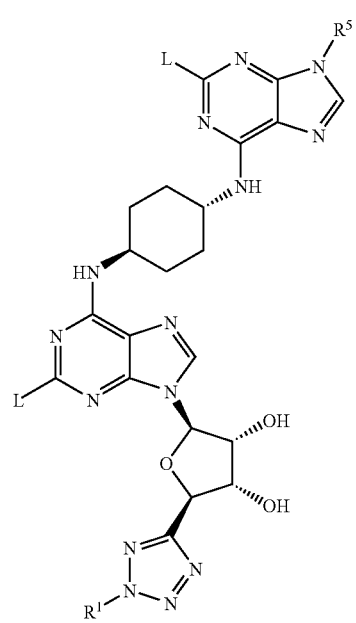

(XIVB)

wherein $R^1$ and $R^5$ are as defined above for compounds of formula (I) and L represents a leaving group;
with a compound of formula (VII), as described above, or a protected derivative thereof:

wherein $R^2$ is as defined above for compounds of formula (I).

L suitably represents halogen, for example bromine or chlorine, in particular chlorine. Said reaction will generally involve heating the reagents to a temperature of 50° C. to 150° C., such as 100° C. to 130° C., particularly about 120° C. to 130° C., in the presence of an inert solvent such as DMSO and a base, such as an amine base (e.g. diisopropylethylamine).

When R⁵ represents hydrogen, the nitrogen to which it is attached (i.e. the 9 position of the purine ring) may suitably be protected, for example as the tetrahydropyran-2-yl derivative. Following the reaction described above for the formation of a protected derivative of a compound of formula (I), the nitrogen may then be deprotected. Suitable conditions for deprotection will depend upon the chosen protecting group, for example, where the protecting group is tetrahydropyran-2-yl suitable deprotection conditions include treatment with formic acid in methanol/water.

Compounds of formula (XIVA) or (XIVB), or protected derivatives thereof, may be prepared by reacting a compound of formula (VI), as described above, or a protected derivative thereof:

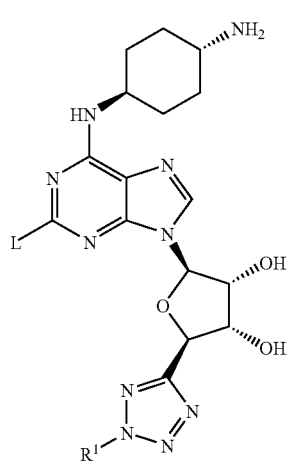
(VI)

wherein R¹ is as defined above for compounds of formula (I) and L represents a leaving group;
with a compound of formula (VA) or (VB), as described above:

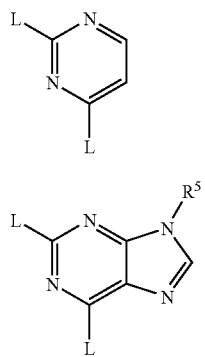
(VA)

(VB)

wherein R⁵ is as defined above for compounds of formula (I) and L represents a leaving group.

As noted above, for compounds of formula (VB) where R⁵ represents hydrogen, the nitrogen to which it is attached (i.e. the 9 position of the purine ring) may suitably be protected, for example as the tetrahydropyran-2-yl derivative.

L suitably represents halogen, for example bromine or chlorine, especially chlorine. The compound of formula (VA) may, for example, be 2,4-dichloropyrimidine. The compound of formula (VB) may, for example, be 2,6-dichloro-9-(tetrahydropyran-2-yl)purine. The reaction will generally be performed in the presence of a base, such as an amine base (e.g. diisopropylethylamine), in a suitable solvent, such as an alcohol (e.g. isopropanol), at an elevated temperature (e.g. 50° C. to 70° C.).

Following the reaction described above for the formation of a protected derivative of a compound of formula (XIVB), the purine nitrogen may be then deprotected. Suitable conditions for deprotection will depend upon the chosen protecting group, for example, where the protecting group is tetrahydropyran-2-yl suitable deprotection conditions include the use of formic acid in methanol/water.

Compounds of formula (IIA), (IIB), (IV), (VI), (VIII), (X), (XIVA) and (XIVB) may be used in a form in which the hydroxyl groups are protected with suitable protecting groups, e.g. with acetonide or acetyl groups, in particular acetyl groups.

As described above protected derivatives of compounds of the invention or intermediates for preparing compounds of the invention may be used. Examples of protecting groups and the means for their removal can be found in T W Greene "Protective Groups in Organic Synthesis" (J Wiley and Sons, 1991). Suitable hydroxyl protecting groups include alkyl (e.g. methyl), acetal (e.g. acetonide) and acyl (e.g. acetyl or benzoyl) which may be removed by hydrolysis, and arylalkyl (e.g. benzyl) which may be removed by catalytic hydrogenolysis. Suitable amine protecting groups include sulphonyl (e.g. tosyl), acyl (e.g. benzyloxycarbonyl or t-butoxycarbonyl) and arylalkyl (e.g. benzyl) which may be removed by hydrolysis or hydrogenolysis as appropriate.

The processes described above for the production of compounds of formula (I) and salts and solvates thereof constitute one aspect of the present invention. Novel intermediates, for example compounds of formulae (IIA), (IIB), (IV), (XIVA), (XIVB) and protected derivatives thereof, also form an aspect of the invention.

The potential for compounds of formula (I) to inhibit leukocyte function may be demonstrated, for example, by their ability to inhibit superoxide (O₂⁻) generation from neutrophils stimulated with chemoattractants such as N-formylmethionyl-leucyl-phenylalanine (fMLP). Accordingly, compounds of formula (I) are of potential therapeutic benefit in providing protection from leukocyte-induced tissue damage in diseases where leukocytes are implicated at the site of inflammation.

Examples of disease states in which the compounds of the invention have potentially beneficial anti-inflammatory effects include diseases of the respiratory tract such as adult respiratory distress syndrome (ARDS), bronchitis (including chronic bronchitis), cystic fibrosis, asthma (including allergen-induced asthmatic reactions), emphysema, rhinitis and septic shock. Other relevant disease states include diseases of the gastrointestinal tract such as intestinal inflammatory diseases including inflammatory bowel disease (e.g. Crohn's disease or ulcerative colitis), *Helicobacter pylori* induced gastritis and intestinal inflammatory diseases secondary to radiation exposure or allergen exposure, and non-steroidal anti-inflammatory drug-induced gastropathy. Furthermore, compounds of the invention may be used to treat skin diseases such as psoriasis, allergic dermatitis and hypersensitivity reactions and diseases of the central nervous system which have an inflammatory component e.g. Alzheimer's disease and multiple sclerosis.

Further examples of disease states in which compounds of the invention have potentially beneficial effects include cardiac conditions such as peripheral vascular disease, post-ischaemic reperfusion injury and idiopathic hypereosinophilic syndrome.

Compounds of the invention which inhibit lymphocyte function may be useful as immunosuppressive agents and so have use in the treatment of auto-immune diseases such as rheumatoid arthritis and diabetes.

Compounds of the invention may also be useful in inhibiting metastasis.

It will be appreciated by those skilled in the art that reference herein to treatment extends to prophylaxis as well as the treatment of established conditions.

More preferably the treatment and/or prophylaxis is of asthma or COPD including chronic bronchitis and emphysema in a mammal (e.g. human).

As mentioned above, compounds of formula (I) are useful in human or veterinary medicine, in particular as anti-inflammatory agents.

There is thus provided as a further aspect of the invention a compound of formula (I) or a pharmaceutically acceptable salt or solvate thereof for use in human or veterinary medicine, particularly in the treatment of patients with an inflammatory condition and/or allergic condition who are susceptible to leukocyte-induced tissue damage.

According to another aspect of the invention, there is provided the use of a compound of formula (I) or a pharmaceutically acceptable salt or solvate thereof for the manufacture of a medicament for the treatment of patients with an inflammatory condition and/or allergic condition who are susceptible to leukocyte-induced tissue damage.

In a further or alternative aspect there is provided a method for the treatment of a human or animal subject with an inflammatory condition and/or allergic condition who is susceptible to leukocyte-induced tissue damage, which method comprises administering to said human or animal subject an effective amount of a compound of formula (I) or a pharmaceutically acceptable salt or solvate thereof.

For use in medicine, the compounds of the present invention are usually administered as a pharmaceutical composition.

The present invention therefore provides in a further aspect a pharmaceutical composition comprising a compound of formula (I) or a pharmaceutically acceptable salt or solvate thereof optionally with one or more pharmaceutically acceptable carriers and/or excipients.

The pharmaceutical composition may be for use in the treatment and/or prophylaxis of any of the conditions described herein.

Compounds of formula (I) and salts and solvates thereof and/or the pharmaceutical composition containing them may be administered, for example, by parenteral (e.g. intravenous, subcutaneous, or intramuscular), inhaled, nasal, transdermal or rectal administration, or as topical treatments (e.g. ointments or gels). Routes of administration of particular interest include inhaled and intra-nasal. Inhaled administration involves topical administration to the lung, e.g. by aerosol or dry powder composition.

The compound of formula (I) and salts and solvates thereof and/or the pharmaceutical composition may be administered by a controlled or sustained release formulation as described in WO 00/50011.

A parenteral composition may comprise a solution or suspension of the compound or pharmaceutically acceptable salt in a sterile aqueous carrier or parenterally acceptable oil. Alternatively, the solution may be lyophilised; the lyophilised parenteral pharmaceutical composition may be reconstituted with a suitable solvent just prior to administration.

Compositions for nasal or inhaled administration may conveniently be formulated as aerosols, solutions, suspensions, drops, gels or dry powders, with aqueous or non-aqueous vehicles optionally with the addition of agents such as thickening agents, buffer salts or acid or alkali to adjust the pH, isotonicity adjusting agents, antioxidants and/or preservatives.

Capsules and cartridges of for example gelatine, or blisters of for example laminated aluminium foil, for use in an inhaler or insufflator may be formulated containing a powder mix of a compound of the invention and a suitable powder base such as lactose or starch.

There is also provided a process for preparing such a pharmaceutical formulation which comprises mixing the ingredients.

For compositions suitable and/or adapted for inhaled administration, the compound or salt or solvate of formula (I) is typically in a particle-size-reduced form, and particularly the size-reduced form is obtained or obtainable by micronization. Generally, the particle size of the size-reduced (e.g. micronised) compound or salt can be defined by a D50 value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomizing device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a chlorofluorocarbon (CFC) or hydrofluorocarbon (HFC). Suitable CFC propellants include dichlorodifluoromethane, trichlorofluoromethane and dichlorotetrafluoroethane. Suitable HFC propellants include 1,1,1,2,3,3,3-heptafluoropropane and 1,1,1,2-tetrafluoroethane. The aerosol dosage forms can also take the form of a pump-atomiser.

Optionally, in particular for dry powder inhalable compositions, a pharmaceutical composition for inhaled administration can be incorporated into a plurality of sealed dose containers (e.g. containing the dry powder composition) mounted longitudinally in a strip or ribbon inside a suitable inhalation device. The container is rupturable or peel-openable on demand and the dose of e.g. the dry powder composition can be administered by inhalation via the device such as the DISKUS™ device, marketed by GlaxoSmithKline. The DISKUS™ inhalation device is for example described in GB 2242134 A, and in such a device at least one container for the pharmaceutical composition in powder form (the container or containers preferably being a plurality of sealed dose containers mounted longitudinally in a strip or ribbon) is defined between two members peelably secured to one another; the device comprises: a means of defining an opening station for the said container or containers; a means for peeling the members apart at the opening station to open the container; and an outlet, communicating with the opened container, through which a user can inhale the pharmaceutical composition in powder form from the opened container. Alternatively, the formulation may be presented if desired together with one or more other therapeutic agents in an inhalation device wherein the individual therapeutic agents are administrable simultaneously but are stored separately (or wholly or partly stored separately for triple combinations), e.g. in separate pharmaceutical compositions, for example as described in WO 03/061743.

The proportion of the active compound of formula (I) or salt or solvate thereof in the topical compositions according to the invention depends on the precise type of formulation to be prepared but may generally be within the range of from 0.001 to 20% by weight, for example 0.001 to 10% by weight.

Generally, however for most types of preparations the proportion used may be within the range of from 0.005 to 1% such as 0.01 to 0.5%. However, in powders for inhalation or insufflation the proportion used may be within the range of from 0.1 to 5%.

Aerosol formulations are preferably arranged so that each metered dose or "puff" of aerosol contains 10 μg-2000 μg, for example 20 μg-2000 μg, preferably about 20 μg-500 μg of a compound of formula (I). Administration may be once daily or several times daily, for example 2, 3, 4 or 8 times, giving for example 1, 2 or 3 doses each time. The overall daily dose with an aerosol will be within the range 20 μg-10 mg, for example 100 μg-10 mg, preferably 200 μg-2000 μg. The overall daily dose and the metered dose delivered by capsules and cartridges in an inhaler or insufflator will generally be double those with aerosol formulations.

The compound (or salts and solvates thereof) and pharmaceutical formulations according to the invention may be used in combination with or include one or more other therapeutic agents, for example selected from anti-inflammatory agents, anticholinergic agents (particularly an $M_1$, $M_2$, $M_1/M_2$ or $M_3$ receptor antagonist), $\beta_2$-adrenoreceptor agonists, antiinfective agents (e.g. antibiotics, antivirals), or antihistamines. The invention thus provides, in a further aspect, a combination comprising a compound of formula (I) or a pharmaceutically acceptable salt, solvate or physiologically functional derivative thereof together with one or more other therapeutically active agents, for example selected from an anti-inflammatory agent (for example a corticosteroid or an NSAID), an anticholinergic agent, a $\beta_2$-adrenoreceptor agonist, an antiinfective agent (e.g. an antibiotic or an antiviral), or an antihistamine. Particular combinations of the invention include a compound of formula (I) or a physiologically acceptable salt or solvate thereof together with a steroid, a $\beta_2$-adrenoreceptor agonist, an anticholinergic, and/or a PDE-4 inhibitor. Preferred combinations are those comprising one or two other therapeutic agents.

It will be clear to a person skilled in the art that, where appropriate, the other therapeutic ingredient(s) may be used in the form of salts, (e.g. as alkali metal or amine salts or as acid addition salts), or prodrugs, or as esters (e.g. lower alkyl esters), or as solvates (e.g. hydrates) to optimise the activity and/or stability and/or physical characteristics (e.g. solubility) of the therapeutic ingredient. It will be clear also that where appropriate, the therapeutic ingredients may be used in optically pure form.

The invention thus provides, in a further aspect, a combination comprising a compound of formula (I) or a pharmaceutically acceptable salt or solvate thereof with one or more other therapeutically active agents, for example, a 2-adrenoreceptor agonist, an anti-histamine, an anti-allergic agent, an anti-inflammatory agent (including a steroid or a PDE-4 inhibitor), an anticholinergic agent or an antiinfective agent (e.g. antibiotics or antivirals).

Examples of $\beta_2$-adrenoreceptor agonists include salmeterol (e.g. as the racemate or a single enantiomer, such as the R-enantiomer), salbutamol (e.g. as the racemate or a single enantiomer such as the R-enantiomer), formoterol (e.g. as the racemate or a single diastereomer such as the R,R-diastereomer), salmefamol, fenoterol, carmoterol, etanterol, naminterol, clenbuterol, pirbuterol, flerobuterol, reproterol, bambuterol, indacaterol or terbutaline and salts thereof, for example the xinafoate (1-hydroxy-2-naphthalenecarboxylate) salt of salmeterol, the sulphate salt or free base of salbutamol or the fumarate salt of formoterol. For example, salmeterol (which may be a racemate or a single enantiomer, such as the R-enantiomer), salbutamol, formoterol, salmefamol, fenoterol or terbutaline and salts thereof, for example the xinafoate salt of salmeterol, the sulphate salt or free base of salbutamol or the fumarate salt of formoterol. Long-acting $\beta_2$-adrenoreceptor agonists, for example those which provide bronchodilation for 12 hours or longer, may be preferred. Examples include salmeterol and formoterol.

Other long acting $\beta_2$-adrenoreceptor agonists include those described in WO02/66422A, WO02/270490, WO02/076933, WO03/024439, WO03/072539, WO 03/091204, WO04/016578, WO04/022547, WO04/037807, WO04/037773, WO04/037768, WO04/039762, WO04/039766, WO01/42193 and WO03/042160.

Particular long-acting $\beta_2$-adrenoreceptor agonists are:

3-(4-{[6-({(2R)-2-hydroxy-2-[4-hydroxy-3-(hydroxymethyl)phenyl]ethyl}amino) hexyl]oxy}butyl)benzenesulfonamide;

3-(3-{[7-({(2R)-2-hydroxy-2-[4-hydroxy-3-hydroxymethyl)phenyl]ethyl}-amino)heptyl]oxy}propyl)benzenesulfonamide;

4-{(1R)-2-[(6-{2-[(2,6-dichlorobenzyl)oxy]ethoxy}hexyl)amino]-1-hydroxyethyl}-2-(hydroxymethyl)phenol;

4-{(1R)-2-[(6-{4-[3-(cyclopentylsulfonyl)phenyl]butoxy}hexyl)amino]-1-hydroxyethyl}-2-(hydroxymethyl)phenol;

N-[2-hydroxyl-5-[(1R)-1-hydroxy-2-[[2-4-[[(2R)-2-hydroxy-2-phenylethyl]amino]phenyl]ethyl]amino]ethyl]phenyl]formamide, N-2{2-[4-(3-phenyl-4-methoxyphenyl)aminophenyl]ethyl}-2-hydroxy-2-(8-hydroxy-2(1H)-quinolinon-5-yl)ethylamine, and 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one, and salts thereof.

The $\beta_2$-adrenoreceptor agonist may be in the form of a salt formed with a pharmaceutically acceptable acid selected from sulphuric, hydrochloric, fumaric, hydroxynaphthoic (for example 1- or 3-hydroxy-2-naphthoic), cinnamic, substituted cinnamic, triphenylacetic, sulphamic, sulphanilic, naphthaleneacrylic, benzoic, 4-methoxybenzoic, 2- or 4-hydroxybenzoic, 4-chlorobenzoic and 4-phenylbenzoic acid.

Anti-inflammatory agents that may be incorporated in a combination include corticosteroids particularly inhaled corticosteroids and their pro-drugs which have anti-inflammatory activity. Examples of corticosteroids include methyl prednisolone, prednisolone, dexamethasone, fluticasone propionate, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester, 6α,9α-difluoro-11β-hydroxy-16α-methyl-17α-(1-methylcylopropylcarbonyl)oxy-3-oxo-androsta-1,4-diene-17β-carbothioic acid S-fluoromethyl ester, 6α,9α-difluoro-11β-hydroxy-16α-methyl-3-oxo-17α-(2,2,3,3-tetramethylcyclopropylcarbonyl)oxy-androsta-1,4-diene-17β-carboxylic acid cyanomethyl ester, beclomethasone esters (such as the 17-propionate ester or the 17,21-dipropionate ester), budesonide, flunisolide, mometasone esters (such as the furoate ester), triamcinolone acetonide, rofleponide, ciclesonide, (16α,17-[[(R)-cyclohexylmethylene]bis (oxy)]-11β,21-dihydroxy-pregna-1,4-diene-3,20-dione), butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester and 6α,9α-difluoro-17α-[(2-furanylcarbonyl)oxy]-11β-hydroxy-16α-methyl-3-oxo-androsta-1,4-diene-17β-carbothioic acid S-fluoromethyl ester, more preferably 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Non-steroidal compounds that may have glucocorticoid activity include those covered in the following patent applications WO03/082827, WO01/10143, WO98/54159, WO04/005229, WO04/009016, WO04/009017, WO04/018429, WO03/104195, WO03/082787, WO03/082280, WO03/

059899, WO03/101932, WO02/02565, WO01/16128, WO00/66590, WO03/086294, WO04/026248, WO03/061651, WO03/08277.

Anti-inflammatory agents include non-steroidal anti-inflammatory drugs (NSAID's).

Possible NSAID's that may be used in a combination include sodium cromoglycate, nedocromil sodium, phosphodiesterase (PDE) inhibitors (for example, theophylline, PDE4 inhibitors or mixed PDE3/PDE4 inhibitors), leukotriene antagonists, inhibitors of leukotriene synthesis (for example, montelukast), iNOS inhibitors, tryptase and elastase inhibitors, beta-2 integrin antagonists and adenosine receptor agonists or antagonists (for example, adenosine 2a agonists), cytokine antagonists (for example, chemokine antagonists, such as a CCR3 antagonist) or inhibitors of cytokine synthesis, or 5-lipoxygenase inhibitors. An iNOS (inducible nitric oxide synthase inhibitor) is preferably for oral administration. Other iNOS inhibitors include those disclosed in WO93/13055, WO98/30537, WO02/50021, WO95/34534 and WO99/62875. Suitable CCR3 inhibitors include those disclosed in WO02/26722.

Phosphodiesterase 4 (PDE4) inhibitors that may be used in a combination include any compound that is known to inhibit the PDE4 enzyme or which is discovered to act as a PDE4 inhibitor, and which are only PDE4 inhibitors, not compounds which inhibit other members of the PDE family, such as PDE3 and PDE5, as well as PDE4.

Compounds include cis-4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl) cyclohexan-1-ol]. Another compound of interest is cis-4-cyano-4-[3-(cyclopentyloxy)-4-methoxyphenyl] cyclohexane-1-carboxylic acid (also known as cilomilast) and its salts, esters, pro-drugs or physical forms, which is described in U.S. Pat. No. 5,552,438 issued 3 Sep., 1996; this patent and the compounds it discloses are incorporated herein in full by reference.

Other PDE4 inhibitors include AWD-12-281 from Elbion (Hofgen, N. et al. 15th EFMC Int Symp Med Chem (September 6-10, Edinburgh) 1998, Abst P.98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (September 19-23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585.

Further compounds are disclosed in the published international patent application WO04/024728 (Glaxo Group Ltd), PCT/EP2003/014867 (Glaxo Group Ltd) and PCT/EP2004/005494 (Glaxo Group Ltd).

Anticholinergic agents are those compounds that act as antagonists at the muscarinic receptors, in particular those compounds which are antagonists of the $M_1$ or $M_3$ receptors, dual antagonists of the $M_1/M_3$ or $M_2/M_3$, receptors or pan-antagonists of the $M_1/M_2/M_3$ receptors. Exemplary compounds for administration via inhalation include ipratropium (for example, as the bromide, CAS 22254-24-6, sold under the name Atrovent), oxitropium (for example, as the bromide, CAS 30286-75-0) and tiotropium (for example, as the bromide, CAS 136310-93-5, sold under the name Spiriva). Also of interest are revatropate (for example, as the hydrobromide, CAS 262586-79-8) and LAS-34273 which is disclosed in WO01/04118. Exemplary compounds for oral administration include pirenzepine (for example, CAS 28797-61-7), darifenacin (for example, CAS 133099-04-4, or CAS 133099-07-7 for the hydrobromide sold under the name Enablex), oxybutynin (for example, CAS 5633-20-5, sold under the name Ditropan), terodiline (for example, CAS 15793-40-5), tolterodine (for example, CAS 124937-51-5, or CAS 124937-52-6 for the tartrate, sold under the name Detrol), otilonium (for example, as the bromide, CAS 26095-59-0, sold under the name Spasmomen), trospium chloride (for example, CAS 10405-02-4) and solifenacin (for example, CAS 242478-37-1, or CAS 242478-38-2, or the succinate also known as YM-905 and sold under the name Vesicare).

Other anticholinergic agents include compounds of formula (XXI), which are disclosed in U.S. patent application 60/487,981:

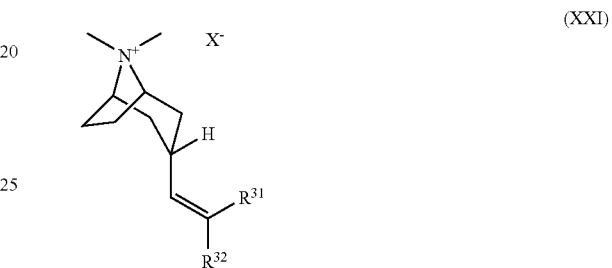

(XXI)

in which the preferred orientation of the alkyl chain attached to the tropane ring is endo; $R^{31}$ and $R^{32}$ are, independently, selected from the group consisting of straight or branched chain lower alkyl groups having preferably from 1 to 6 carbon atoms, cycloalkyl groups having from 5 to 6 carbon atoms, cycloalkyl-alkyl having 6 to 10 carbon atoms, 2-thienyl, 2-pyridyl, phenyl, phenyl substituted with an alkyl group having not in excess of 4 carbon atoms and phenyl substituted with an alkoxy group having not in excess of 4 carbon atoms;

$X^-$ represents an anion associated with the positive charge of the N atom. $X^-$ may be but is not limited to chloride, bromide, iodide, sulfate, benzene sulfonate, and toluene sulfonate, including, for example:

(3-endo)-3-(2,2-di-2-thienylethenyl)-8,8-dimethyl-8-azoniabicyclo[3.2.1]octane bromide;

(3-endo)-3-(2,2-diphenylethenyl)-8,8-dimethyl-8-azoniabicyclo[3.2.1]octane bromide;

(3-endo)-3-(2,2-diphenylethenyl)-8,8-dimethyl-8-azoniabicyclo[3.2.1]octane 4-methylbenzenesulfonate;

(3-endo)-8,8-dimethyl-3-[2-phenyl-2-(2-thienyl)ethenyl]-8-azoniabicyclo[3.2.1]octane bromide; and/or (3-endo)-8,8-dimethyl-3-[2-phenyl-2-(2-pyridinyl)ethenyl]-8-azoniabicyclo[3.2.1]octane bromide.

Further anticholinergic agents include compounds of formula (XXII) or (XXIII), which are disclosed in U.S. patent application 60/511,009:

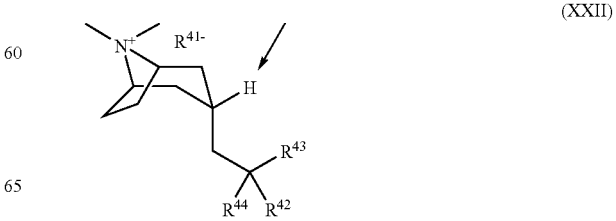

(XXII)

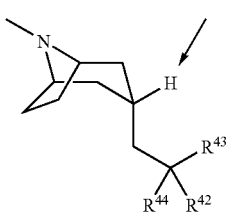

(XXIII)

wherein:
the H atom indicated is in the exo position;
$R^{41-}$ represents an anion associated with the positive charge of the N atom. R1⁻ may be but is not limited to chloride, bromide, iodide, sulfate, benzene sulfonate and toluene sulfonate;
$R^{42}$ and $R^{43}$ are independently selected from the group consisting of straight or branched chain lower alkyl groups (having preferably from 1 to 6 carbon atoms), cycloalkyl groups (having from 5 to 6 carbon atoms), cycloalkyl-alkyl (having 6 to 10 carbon atoms), heterocycloalkyl (having 5 to 6 carbon atoms) and N or O as the heteroatom, heterocycloalkyl-alkyl (having 6 to 10 carbon atoms) and N or O as the heteroatom, aryl, optionally substituted aryl, heteroaryl, and optionally substituted heteroaryl;
$R^{44}$ is selected from the group consisting of $(C_1-C_6)$alkyl, $(C_3-C_{12})$cycloalkyl, $(C_3-C_7)$heterocycloalkyl, $(C_1-C_6)$alkyl$(C_3-C_{12})$cycloalkyl, $(C_1-C_6)$alkyl$(C_3-C_7)$heterocycloalkyl, aryl, heteroaryl, $(C_1-C_6)$alkyl-aryl, $(C_1-C_6)$alkyl-heteroaryl, —$OR^{45}$, —$CH_2OR^{45}$, —$CH_2OH$, —CN, —$CF_3$, —$CH_2O(CO)R^{46}$, —$CO_2R^{47}$, —$CH_2NH_2$, —$CH_2N(R^{47})SO_2R^{45}$, —$SO_2N(R^{47})(R^{48})$, —$CON(R^{47})(R^{48})$, —$CH_2N(R^{48})CO(R^{46})$, —$CH_2N(R^{48})SO_2(R^{46})$, —$CH_2N(R^{48})CO_2(R^{45})$, $CH_2N(R^{48})CONH(R^{47})$;
$R^{45}$ is selected from the group consisting of $(C_1-C_6)$alkyl, $(C_1-C_6)$alkyl$(C_3-C_{12})$cycloalkyl, $(C_1-C_6)$alkyl$(C_3-C_7)$heterocycloalkyl, $(C_1-C_6)$alkyl-aryl, $(C_1-C_6)$alkyl-heteroaryl;
$R^{46}$ is selected from the group consisting of $(C_1-C_6)$alkyl, $(C_3-C_{12})$cycloalkyl, $(C_3-C_7)$heterocycloalkyl, $(C_1-C_6)$alkyl$(C_3-C_{12})$cycloalkyl, $(C_1-C_6)$alkyl$(C_3-C_7)$heterocycloalkyl, aryl, heteroaryl, $(C_1-C_6)$alkyl-aryl, $(C_1-C_6)$alkyl-heteroaryl;
$R^{47}$ and $R^{48}$ are, independently, selected from the group consisting of H, $(C_1-C_6)$alkyl, $(C_3-C_{12})$cycloalkyl, $(C_3-C_7)$heterocycloalkyl, $(C_1-C_6)$alkyl$(C_3-C_{12})$cycloalkyl, $(C_1-C_6)$alkyl$(C_3-C_7)$heterocycloalkyl, $(C_1-C_6)$alkyl-aryl, and $(C_1-C_6)$alkyl-heteroaryl, including, for example:
(endo)-3-(2-methoxy-2,2-di-thiophen-2-yl-ethyl)-8,8-dimethyl-8-azonia-bicyclo[3.2.1]octane iodide;
3-((endo)-8-methyl-8-aza-bicyclo[3.2.1]oct-3-yl)-2,2-diphenyl-propionitrile;
(endo)-8-methyl-3-(2,2,2-triphenyl-ethyl)-8-aza-bicyclo[3.2.1]octane;
3-((endo)-8-methyl-8-aza-bicyclo[3.2.1]oct-3-yl)-2,2-diphenyl-propionamide;
3-((endo)-8-methyl-8-aza-bicyclo[3.2.1]oct-3-yl)-2,2-diphenyl-propionic acid;
(endo)-3-(2-cyano-2,2-diphenyl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane bromide;
3-((endo)-8-methyl-8-aza-bicyclo[3.2.1]oct-3-yl)-2,2-diphenyl-propan-1-ol;
N-benzyl-3-((endo)-8-methyl-8-aza-bicyclo[3.2.1]oct-3-yl)-2,2-diphenyl-propionamide;
(endo)-3-(2-carbamoyl-2,2-diphenyl-ethyl)-8,8-dimethyl-8-azonia-bicyclo[3.2.1]octane iodide;
1-benzyl-3-[3-((endo)-8-methyl-8-aza-bicyclo[3.2.1]oct-3-yl)-2,2-diphenyl-propyl]-urea;
1-ethyl-3-[3-((endo)-8-methyl-8-aza-bicyclo[3.2.1]oct-3-yl)-2,2-diphenyl-propyl]-urea;
N-[3-((endo)-8-methyl-8-aza-bicyclo[3.2.1]oct-3-yl)-2,2-diphenyl-propyl]-acetamide;
N-[3-((endo)-8-methyl-8-aza-bicyclo[3.2.1]oct-3-yl)-2,2-diphenyl-propyl]-benzamide;
3-((endo)-8-methyl-8-aza-bicyclo[3.2.1]oct-3-yl)-2,2-di-thiophen-2-yl-propionitrile;
(endo)-3-(2-cyano-2,2-di-thiophen-2-yl-ethyl)-8,8-dimethyl-8-azonia-bicyclo[3.2.1]octane iodide;
N-[3-((endo)-8-methyl-8-aza-bicyclo[3.2.1]oct-3-yl)-2,2-diphenyl-propyl]-benzenesulfonamide;
[3-((endo)-8-methyl-8-aza-bicyclo[3.2.1]oct-3-yl)-2,2-diphenyl-propyl]-urea;
N-[3-((endo)-8-methyl-8-aza-bicyclo[3.2.1]oct-3-yl)-2,2-diphenyl-propyl]-methanesulfonamide; and/or
(endo)-3-{2,2-diphenyl-3-[(1-phenyl-methanoyl)-amino]-propyl}-8,8-dimethyl-8-azonia-bicyclo[3.2.1]octane bromide.
Further compounds include:
(endo)-3-(2-methoxy-2,2-di-thiophen-2-yl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane bromide;
(endo)-3-(2-carbamoyl-2,2-diphenyl-ethyl)-8,8-dimethyl-8-azonia-bicyclo[3.2.1]octane iodide;
(endo)-3-(2-cyano-2,2-di-thiophen-2-yl-ethyl)-8,8-dimethyl-8-azonia-bicyclo[3.2.1]octane iodide; and/or
(endo)-3-{2,2-diphenyl-3-[(1-phenyl-methanoyl)-amino]-propyl}-8,8-dimethyl-8-azonia-bicyclo[3.2.1]octane bromide.

Antihistamines (also referred to as H1-receptor antagonists) include any one or more of the numerous antagonists known which inhibit H1-receptors, and are safe for human use. First generation antagonists, include derivatives of ethanolamines, ethylenediamines, and alkylamines, such as diphenylhydramine, pyrilamine, clemastine, chlorpheniramine. Second generation antagonists, which are non-sedating, include loratidine, desloratidine, terfenadine, astemizole, acrivastine, azelastine, levocetirizine fexofenadine, cetirizine and efletirizine.

The invention thus provides, in a further aspect, a combination comprising a compound of formula (I) or a pharmaceutically acceptable salt or solvate thereof together with a PDE4 inhibitor.

The invention thus provides, in a further aspect, a combination comprising a compound of formula (I) or a pharmaceutically acceptable salt or solvate thereof together with a β2-adrenoreceptor agonist.

The invention thus provides, in a further aspect, a combination comprising a compound of formula (I) or a pharmaceutically acceptable salt or solvate thereof together with an anticholinergic.

The invention thus provides, in a further aspect, a combination comprising a compound of formula (I) or a pharmaceutically acceptable salt or solvate thereof together with an antihistamine.

The combinations referred to above may conveniently be presented for use in the form of a pharmaceutical formulation and thus pharmaceutical formulations comprising a combination as defined above together with a pharmaceutically acceptable diluent or carrier represent a further aspect of the invention.

The individual compounds of such combinations may be administered either sequentially or simultaneously in separate or combined pharmaceutical formulations. Preferably, the individual compounds will be administered simultaneously in a combined pharmaceutical formulation. Appropriate doses of known therapeutic agents will be readily appreciated by those skilled in the art.

The combinations referred to above may conveniently be presented for use in the form of a pharmaceutical composition and thus a pharmaceutical composition comprising a combination as defined above optionally together with one or more pharmaceutically acceptable carriers and/or excipients represent a further aspect of the invention.

The individual compounds of such combinations may be administered either sequentially or simultaneously in separate or in combined pharmaceutical compositions.

The combinations referred to above may conveniently be presented for use in the form of a pharmaceutical formulation and thus pharmaceutical formulations comprising a combination as defined above together with a pharmaceutically acceptable diluent or carrier represent a further aspect of the invention.

The compounds of the invention may be more efficacious, show greater selectivity, have fewer side effects, have a longer duration of action, show less systemic activity when administered by inhalation or have other more desirable properties than similar known compounds.

In particular the compounds of the invention may be highly potent at the $A_{2A}$ receptor, show greater selectivity for the adenosine $2_A$ receptor subtype over other adenosine receptor subtypes (especially the $A_1$ and $A_3$ receptor subtypes), be capable of being highly bound to human serum albumin (greater than about 90%) and/or may exhibit less pronounced cardiac effects than hitherto known compounds.

The various aspects of the invention will now be described by reference to the following Examples. These Examples are merely illustrative and are not to be construed as a limitation of the scope of the present invention.

EXAMPLES

Synthetic Examples

General Experimental Details

All reactions were carried out under an atmosphere of nitrogen unless specified otherwise All temperatures are given in degrees centigrade.

Where products were purified by column chromatography, 'flash silica' refers to silica gel for chromatography, 0.035 to 0.070 mm (220 to 440 mesh) (e.g. Fluka silica gel 60), where column elution was accelerated by an applied pressure of nitrogen at up to 10 p.s.i. Where thin layer chromatography (TLC) has been used, it refers to silica gel TLC using plates, typically 4×10 cm silica gel on aluminium foil plates with a fluorescent indicator (254 nm), (e.g. Fluka 60778). Biotage refers to prepacked silica gel cartridges containing KP-Sil run on a flash 12i chromatography module. Solid Phase Extraction (SPE) columns are pre-packed cartridges used in parallel purifications, normally under vacuum. These are commercially available from Varian. SCX cartridges are Ion Exchange SPE columns where the stationary phase is polymeric benzene sulfonic acid. These are used to isolate amines.

The Liquid Chromatography/Mass Spectrometry (LC/MS) systems used:

LCMS was conducted on Phenomenex Luna 3 micron C18(2) 30×4.6 mm column eluting with 0.1% $HCO_2H$ in water (solvent A) and 0.1% $HCO_2H$ in acetonitrile (solvent B), using the following elution gradient:

0-0.5 min 5% B, 0.5-4.5 min 5-95% B, 4.5-5.5 min 95% B, 5.5-6.0 min 95-5% B at a flow rate of 2 mL/min. The mass spectra were recorded on a Micromass Platform LC quadrupole mass spectrometer using electro spray positive and negative mode (ES+ve and ES−ve).

For the alternative preparations of Examples 2, 4 and 7, the LC/MS was conducted on a Supelcosil LCABZ+PLUS column (3.3 cm×4.6 mm ID) eluting with 0.1% $HCO_2H$ and 0.01M ammonium acetate in water (solvent A) and 0.05% $HCO_2H$ 5% water in acetonitrile (solvent B), using the following elution gradient 0.0-7 min 0% B, 0.7-4.2 min 100% B, 4.2-5.3 min 0% B, 5.3-5.5 min 0% B at a flow rate of 3 ml/min. The mass spectra were recorded on a Fisons VG Platform spectrometer using electrospray positive and negative mode (ES+ve and ES−ve).

Preparative HPLC Conditions:

Where products were purified by preparative HPLC, this was carried out on a Genesis C18 reverse-phase column with 7 micron packing and of dimension 21 mm id×100 mm. Elution was carried out on a gradient of MeOH: Water, buffered with 0.1% formic acid, starting at 5% MeOH and increasing the MeOH at 1% per minute until the compound had eluted. The concentration of the MeOH in the eluent at the time of elution was 20-30%. The flow rate was 5 mL/min and UV detection at 254 nm was used.

NMR:

$^1$H NMR spectra were recorded using a Bruker DPX 250 MHz, referenced to tetramethylsilane.

ISCO Companion XL:

The Companion XL is an automated single user flash chromatography system which utilises disposable cartridges (120 gm to 1500 gm). It provides binary on-line solvent mixing to enable gradient methods to be run. Samples are logged in using the multi functional open access software which manages flow rates, gradient profile and collection conditions. The system is equipped with a variable wavelength uv detector and two Foxy 200 fraction collectors enabling automated peak cutting, collection and tracking.

| Abbreviations used: | |
|---|---|
| IPA | isopropanol |
| DCM | dichloromethane |
| THF | tetrahydofuran |
| MeOH | methanol |
| DMF | dimethylformamide |
| DIPEA | diisopropylethylamine |
| EtOAc | ethyl acetate |
| ACN | acetonitrile |
| CHC | cyclohexane |
| DMSO | dimethylsulphoxide |
| DMAP | 4-dimethylaminopyridine |
| HATU | O-(7-Azabenzotriazol-1-yl)-N,N,N', N'-tetramethyluronium hexafluorophosphate |
| NBS | N-bromosuccinimde |
| IMS and IMS-G | industrial methylated spirit |
| TFA | trifluoroacetic acid |
| Boc | tert-butyloxycarbonyl |
| Rt | retention time |
| h | hour(s) |
| min | minute(s) |
| HPLC | High pressure liquid chromatography |
| K | Kelvin |
| TBME | tertiary butyl methyl ether |
| NMR | nuclear magnetic resonance |

Flash silica gel refers to Merck ART No. 9385; silica gel refers to Merck ART No. 7734

Amine Starting Materials:

The amine in Examples 1 and 6 is commercially available from, for example, Sigma.

The amine in Examples 2 and 7 was used as the free base. The free base may be derived from the dihydrochloride salt which is commercially available from, for example. Sigma. Preparation of the free base is described in, for example, Intermediate 5 below.

The amine in Examples 3 and 8 may be prepared by, for example, the method describe in J. Het. Chem., (1981), 18(4), 831 to 832.

The amine in Examples 4 and 9 is commercially available from, for example, Apin.

The amine in Examples 5 and 10 is commercially available from, for example, Aldrich.

Intermediate 1

(2R,3R,4R,5R)-2-(2-Chloro-6-{[trans-4-({[(1,1-dimethylethyl)oxy]carbonyl}amino)cyclohexyl]amino}-9H-purin-9-yl)-5-(2-ethyl-2H-tetrazol-5-yl)tetrahydrofuran-3,4-diyl diacetate

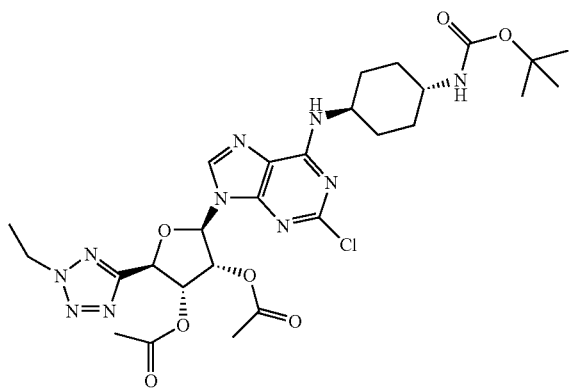

To stirred (2R,3R,4R,5R)-2-(2,6-dichloro-9H-purin-9-yl)-5-(2-ethyl-2H-tetrazol-5-yl)tetrahydrofuran-3,4-diyl diacetate (ref WO98/28319A1) (15 g) in propan-2-ol (100 ml) was added N,N-diisopropylethylamine (7.7 ml) and 1,1-dimethylethyl(trans-4-aminocyclohexyl)carbamate (6.82 g). The mixture was stirred at 65° C. for 24 h before cooling to room temperature and concentrating in vacuo. The crude product was purified by column chromatography (silica) eluting with 30% cyclohexane in ethyl acetate. The appropriate fractions were combined and concentrated in vacuo and triturated with diethyl ether to yield the title compound as a white solid, 8.56 g.

LC-MS: Rt 3.88 min.

Alternative Preparation of Intermediate 1

(2R,3R,4R,5R)-2-(2,6-Dichloro-9H-purin-9-yl)-5-(2-ethyl-2H-tetrazol-5-yl)tetrahydrofuran-3,4-diyl diacetate (10 g) (ref WO98/28319A1) was suspended in isopropanol (100 ml). 1,1-Dimethylethyl(trans-4-aminocyclohexyl)carbamate (4.56 g) and N,N-diisopropylethylamine (5.6 ml) were added and the mixture heated at 65° C. under nitrogen overnight. The reaction mixture was allowed to cool to room temperature and evaporated down in vacuo. The residue was partitioned between ethyl acetate and water. The organic phase was separated and the aqueous extracted twice with ethyl acetate. The organic phases were combined, washed with water, dried (Na$_2$SO$_4$), and evaporated down in vacuo, dried under high vacuum overnight, to give the title compound, 12.49 g.

LCMS; Rt 3.38 min, MH$^+$ 649.

Intermediate 2

(2R,3R,4R,5R)-2-[2-Chloro-6-[(trans-4-{[2-chloro-9-(tetrahydro-2H-pyran-2-yl)-9H-purin-6-yl]amino}cyclohexyl)amino]-9H-purin-9-yl]-5-(2-ethyl-2H-tetrazol-5-yl)tetrahydrofuran-3,4-diyl diacetate (2R,3R,4R,5R)-2-(2-Chloro-6-{[trans-4-({[(1,1-dimethylethyl)oxy]carbonyl}amino)cyclohexyl]amino}-9H-purin-9-yl)-5-(2-ethyl-2H-tetrazol-5-yl)tetrahydrofuran-3,4-diyl diacetate (Intermediate 1) (5.2 mmol) was treated with 1:1 trifluoroacetic acid/dichloromethane (20 ml) for ca. 2 h. This was concentrated in vacuo and the residue was purified by SPE (SCX, 50 g), eluting sequentially with dichloromethane, methanol, 40% (2M ammonia in methanol): dichloromethane and 2M ammonia in methanol. The appropriate fraction was concentrated in vacuo and suspended in propan-2-ol (60 ml). To this was added N,N-diisopropylethylamine (4 m. eq.) and 2,6-dichloro-9-(tetrahydro-2H-pyran-2-yl)-9H-purine (prepared according to the method disclosed in WO2003080604A1) (1 m. eq.) and this was heated at 60° C. overnight. After cooling to room temperature, further 2,6-dichloro-9-(tetrahydro-2H-pyran-2-yl)-9H-purine (0.5 m. eq.) and N,N-diisopropylethylamine (4 ml) were added and this was heated at 60° C. for a further ca. 5 h. After cooling to room temperature, the reaction mixture was then concentrated in vacuo and the residue was partitioned between dichloromethane (ca. 60 ml) and water (ca. 60 ml). The organics were washed with water (ca. 60 ml), dried over magnesium sulfate and concentrated in vacuo to yield the title compound as an off-white crystalline solid, 4 g.

LC-MS: Rt 3.67 min.

Alternative Preparation of Intermediate 2

(2R,3R,4R,5R)-2-{6-[(trans-4-Aminocyclohexyl)amino]-2-chloro-9H-purin-9-yl}-5-(2-ethyl-2H-tetrazol-5-yl)tetrahydrofuran-3,4-diyl diacetate (Intermediate 4) (7.9 g) was dissolved in isopropanol (200 ml) and stirred at room temperature under nitrogen. N,N-diisopropylethylamine (10 ml) was added followed by 2,6-dichloro-9-(tetrahydro-2H-pyran-2-yl)-9H-purine (3.92 g). The mixture was stirred at 60° C. under nitrogen for 18 h. The reaction mixture was allowed to cool to room temperature and evaporated down in vacuo. The residue was partitioned between ethyl acetate and water. The organic phase was separated and the aqueous extracted twice with ethyl acetate. The organic phases were combined, dried (MgSO$_4$), and evaporated down in vacuo to give the title compound (10.35 g). Used without purification.

LCMS; Rt 3.44 min, (MH)$^+$ 785.

Intermediate 3

(2R,3R,4R,5R)-2-[2-Chloro-6-({trans-4-[(2-chloro-4-pyrimidinyl)amino]cyclohexyl}amino)-9H-purin-9-yl]-5-(2-ethyl-2H-tetrazol-5-yl)tetrahydrofuran-3,4-diyl diacetate

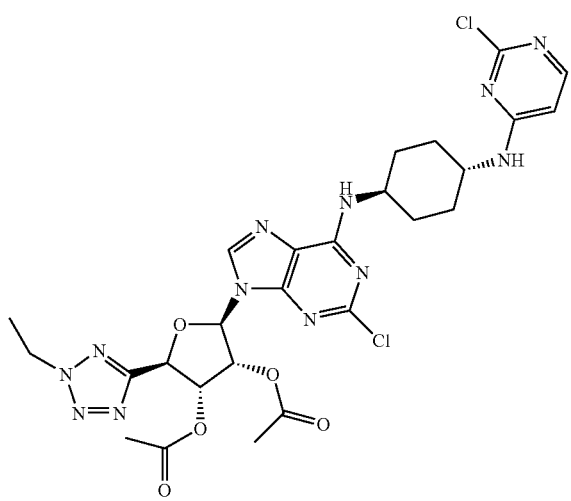

(2R,3R,4R,5R)-2-(2-Chloro-6-{[trans-4-({[(1,1-dimethylethyl)oxy]carbonyl}amino)cyclohexyl]amino}-9H-purin-9-yl)-5-(2-ethyl-2H-tetrazol-5-yl)tetrahydrofuran-3,4-diyl diacetate (Intermediate 1) (5.4 mmol) was treated with 1:1 trifluoroacetic acid/dichloromethane (20 ml) at room temperature for ca. 1 h. This was concentrated in vacuo and the residue was partitioned between dichloromethane (50 ml) and aqueous sodium bicarbonate (50 ml). The organics were washed with aqueous sodium bicarbonate (50 ml), dried over sodium sulfate and concentrated in vacuo to give a white solid. This was dissolved in propan-2-ol (100 ml). To this was added N,N-diisopropylethylamine (4 m. eq.) and 2,4-dichloropyrimidine (1 m. eq.). The reaction mixture was heated at 60° C. overnight. The reaction mixture was concentrated in vacuo and the residue was partitioned between ethyl acetate (50 ml) and water (50 ml). The organics were washed with water (50 ml), dried over sodium sulfate and concentrated in vacuo. The crude product was purified by SPE (50 g, silica) eluting with x% ethyl acetate in dichloromethane where x=25, 50, 75. Fractions containing desired product were combined and concentrated in vacuo to yield the title compound as a colourless gum, 1.49 g.

LC-MS: Rt 3.44 min.

Alternative Preparation of Intermediate 3

(2R,3R,4R,5R)-2-{6-[(trans-4-Aminocyclohexyl)amino]-2-chloro-9H-purin-9-yl}-5-(2-ethyl-2H-tetrazol-5-yl)tetrahydrofuran-3,4-diyl diacetate (Intermediate 4) (3.2 g) was dissolved in isopropanol (100 ml) and stirred at room temperature under nitrogen. N,N-diisopropylethylamine (4 ml) was added followed by 2,4-dichloropyrimidine (0.86 g). The mixture was heated at 60° C. for 18 h. The reaction mixture was allowed to cool to room temperature and evaporated down in vacuo. The residue was partitioned between ethyl acetate and water. The organic phase was separated and the aqueous extracted twice with ethyl acetate. The organic phases were combined, dried (MgSO$_4$), and evaporated down in vacuo. The residue was purified on a silica SPE cartridge (100 g), eluting with 0 to 100% ethyl acetate—dichloromethane gradient over 60 min. The appropriate fractions were combined and evaporated down in vacuo to give the title compound, 1.53 g.

LCMS; Rt 3.24 min, MH+ 661.

Intermediate 4

(2R,3R,4R,5R)-2-{6-[(trans-4-Aminocyclohexyl)amino]-2-chloro-9H-Purin-9-yl}-5-(2-ethyl-2H-tetrazol-5-yl)tetrahydrofuran-3,4-diyl diacetate

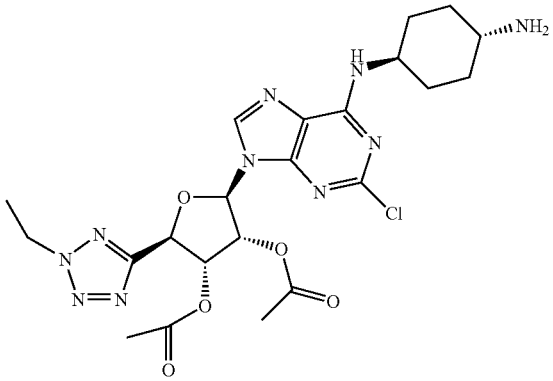

(2R,3R,4R,5R)-2-(2-Chloro-6-{[trans-4-({[(1,1-dimethylethyl)oxy]carbonyl}amino)cyclohexyl]amino}-9H-purin-9-yl)-5-(2-ethyl-2H-tetrazol-5-yl)tetrahydrofuran-3,4-diyl diacetate (Intermediate 1) (12.49 g), was dissolved in trifluoroacetic acid—dichloromethane mixture (50:50; 40 ml). The mixture was stirred at room temperature for 1-2 h and then evaporated down in vacuo. The residue was partitioned between ethyl acetate and 2N aq.sodium bicarbonate solution, making sure the trifluoroacetic acid was neutralised. The organic phase was separated, washed with brine, dried (MgSO$_4$), and evaporated down in vacuo, to give the title compound, 11.2 g.

LCMS; Rt 2.3 min, MH+ 549.

Intermediate 5

[2-(1-Methyl-1H-imidazol-4-yl)ethyl]amine

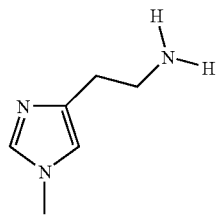

a) 7,8-Dihydroimidazo[1,5-c]pyrimidin-5(6H)-one

Carbonyldiimidazole (970.2 g) was added to a stirred suspension of [2-(1-methyl-1H-imidazol-4-yl)ethyl]amine dihydrochloride (999.9 g) (commercial eg Sigma) and imidazole (37 g) in dichloromethane (5.3 litres) at ca 22° C. The resulting white suspension was heated at reflux until reaction was complete by nmr (4 h.). Solvent (8 litres) was distilled off at atmospheric pressure whilst adding IMS-G (8 litres). Additional IMS-G (2 litres) was added and the suspension cooled to ca. 22° C. and aged at this temperature for at 2 h. The solid was collected by filtration, washed with IMS-G (2×0.5 litres), pulled dry and dried in vacuo at ca. 60° C. to yield the title compound, 478 g.

NMR (d6-DMSO) 300K: 8.22δ (1H, br.s), 8.06δ (1H, s), 6.80δ (1H, s), 3.35δ (2H, m), 2.87δ (2H, m).

b) 2-Methyl-5-oxo-5,6,7,8-tetrahydroimidazo[1,5-c]pyrimidin-2-ium 4-methylbenzenesulfonate

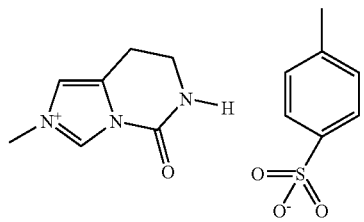

A stirred suspension of 7,8-dihydroimidazo[1,5-c]pyrimidin-5(6H)-one (699.7 g) in DMF 2.45 litres) was heated to ca. 60° C. A solution of methyl 4-methylbenzenesulfonate (1058.2 g.) in DMF (0.7 litres) was added over 100 min at ca. 60° C., and rinsed in with DMF (0.35 litres). The white suspension was stirred at ca. 60° C. for 200 min. when the reaction was complete by nmr. The reaction mixture was allowed to cool to ca. 40° C. and TBME (5.25 litres) was added. The product was cooled to ca. 22° C., aged at this temperature for 17 h, and filtered. The cake was washed with TBME-DMF (3:1, 1.4 litres), then with TBME (2×1.4 litres), the cake was pulled dry, and the product was dried in vacuo at ca. 50° C. to yield the title compound, 1583.5 g.

NMR (d6-DMSO) 300K: 9.83δ (1H, s), 9.04δ (1H, br. s), 7.59δ (1H, s), 7.48δ (2H, d), 7.11δ (2H, d), 3.89δ (3H, s), 3.46δ (2H, m), 3.00δ (2H, t), 2.29δ (3H, s).

c) [2-(1-methyl-1H-imidazol-4-yl)ethyl]amine bis(4-methylbenzenesulfonate)

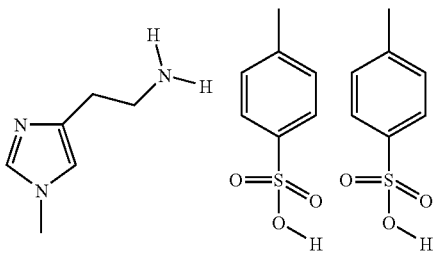

A mixture of 2-methyl-5-oxo-5,6,7,8-tetrahydroimidazo[1,5-c]pyrimidin-2-ium 4-methylbenzenesulfonate (625.1 g), 4-methylbenzenesulfonic acid hydrate (406.6 g), 1,4-dioxan (9.38 litres) and water (625 ml) was heated at reflux (ca. 90° C.) for 2.5 h. when the reaction was complete by nmr. The reaction mixture was concentrated by distillation at atmospheric pressure collecting 7.03 litres. The concentrate was allowed to cool to ca. 77° C., and IMS-G (1.56 litres) was added. The resulting bright solution was allowed to cool and was seeded with [2-(1-methyl-1H-imidazol-4-yl)ethyl]amine bis(4-methylbenzenesulfonate) (0.625 g) at ca. 54° C. The suspension was allowed to cool to ca. 22° C. and aged for 40 min. The solid was filtered off and washed successively with 1,4-dioxan-IMS (3:1, 1.25 litres), and then 1,4-dioxan (2×1.25 litres), pulled dry and dried in vacuo at ca. 50° C. to yield the title compound, 866.3 g.

NMR (d6-DMSO) 300K: 8.80δ (1H, s), 7.69δ (4H, d), 7.45δ (1H, s), 7.25δ (4H, d), 3.87δ (3H, s), 3.26δ (2H, t), 3.09δ (2H, t), 2.36δ (6H, s).

d) [2-(1-methyl-1H-imidazol-4-yl)ethyl]amine

[2-(1-methyl-1H-imidazol-4-yl)ethyl]amine bis(4-methylbenzenesulfonate) (50 g) was dissolved in IMS (200 ml)/water (200 ml). This was passed through a DOWEX550A column (600 g), eluting with IMS (ca. 4 litres). Appropriate fractions were combined and concentrated in vacuo to yield the title compound, 13.4 g.

NMR (CDCl3) 298K: 7.34δ (1H, s), 6.66δ (1H, s), 3.63δ (3H, s), 2.97δ (2H, t), 2.69δ (2H, t).

Example 1

(2R,3S,4R,5R)-2-(2-Ethyl-2H-tetrazol-5-yl)-5-[2-{[2-(1H-imidazol-4-yl)ethyl]amino}-6-({trans-4-[(2-{[2-(1H-imidazol-4-yl)ethyl]amino-1H-purin-6-yl)amino]cyclohexyl}amino)-9H-purin-9-yl]tetrahydro-3,4-furandiol, triformate

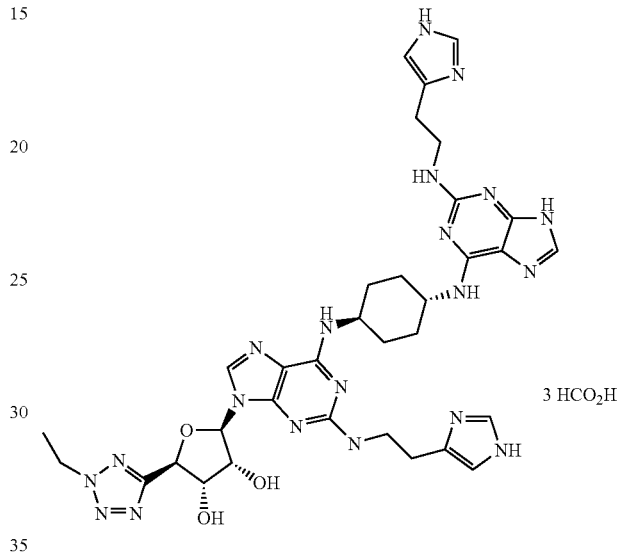

A mixture of (2R,3R,4R,5R)-2-{2-chloro-6-[(trans-4-{[2-chloro-9-(tetrahydro-2H-pyran-2-yl)-9H-purin-6-yl]amino}cyclohexyl)amino]-9H-purin-9-yl}-5-(2-ethyl-2H-tetrazol-5-yl)tetrahydrofuran-3,4-diyl diacetate (Intermediate 2) (0.19 mmole), amine (histamine) (20 m. eq.) and N,N-diisopropylethylamine (20 m. eq.) in dimethylsulfoxide (1 ml) was heated at 125° C. overnight. The cooled reaction mixture was washed with tert-butyl methyl ether (2×ca. 10 ml), dissolved in methanol (2 ml)/water (4 ml)/formic acid (0.5 ml) and heated with a heat gun. It was purified by preparative hplc to give the title compound as an off-white solid, 58 mg.

LC-MS: Rt 4.41 min, MH$^+$=767.

Examples 2, 3, 4 and 5 were synthesised in an analogous manner to Example 1:

| Example | Amine | Product | Product mass | LC-MS Rt | MH+ |
|---|---|---|---|---|---|
| 2 | ![amine structure] | (2R,3S,4R,5R)-2-(2-ethyl-2H-tetrazol-5-yl)-5-[2-{[2-(1-methyl-1H-imidazol-4-yl)ethyl]amino}-6-({trans-4-[(2-{[2-(1-methyl-1H-imidazol-4-yl)ethyl]amino}-1H-purin-6-yl)amino]cyclohexyl}amino)-9H-purin-9-yl]tetrahydro-3,4-furandiol, diformate | 45 mg | 4.41 min | 795 |

-continued

| Example | Amine | Product | Product mass | LC-MS Rt | MH+ |
|---|---|---|---|---|---|
| 3 | | (2R,3S,4R,5R)-2-(2-ethyl-2H-tetrazol-5-yl)-5-[2-{[2-(5-methyl-1H-imidazol-4-yl)ethyl]amino}-6-({trans-4-[(2-{[2-(5-methyl-1H-imidazol-4-yl)ethyl]amino}-1H-purin-6-yl)amino]cyclohexyl}amino)-9H-purin-9-yl]tetrahydro-3,4-furandiol, triformate | 74 mg | 4.60 min | 795 |
| 4 | | (2R,3S,4R,5R)-2-(2-ethyl-2H-tetrazol-5-yl)-5-[2-{[4-(1-pyrrolidinyl)butyl]amino}-6-({trans-4-[(2-{[4-(1-pyrrolidinyl)butyl]amino}-1H-purin-6-yl)amino]cyclohexyl}amino)-9H-purin-9-yl]tetrahydro-3,4-furandiol, triformate | 40 mg | 4.56 min | 829 |
| 5 | | (2R,3S,4R,5R)-2-(2-[(trans-4-aminocyclohexyl)amino]-6-{[trans-4-({2-[(trans-4-aminocyclohexyl)amino]-9H-purin-6-yl}amino)cyclohexyl]amino}-9H-purin-9-yl)-5-(2-ethyl-2H-tetrazol-5-yl)tetrahydro-3,4-furandiol, triformate | 55 mg | 4.38 min | 773 |

*in Example 2 the amine was used as the free base which may be derived from the commercially available dihydrochloride salt.

Example 6

(2R,3S,4R,5R)-2-(2-Ethyl-2H-tetrazol-5-yl)-5-[2-{[2-(1H-imidazol-4-yl)ethyl]amino}-6-({trans-4-[(2-{[2-(1H-imidazol-4-yl)ethyl]amino}-4-pyrimidinyl)amino]cyclohexyl}amino)-9H-purin-9-yl]tetrahydro-3,4-furandiol, tetraformate

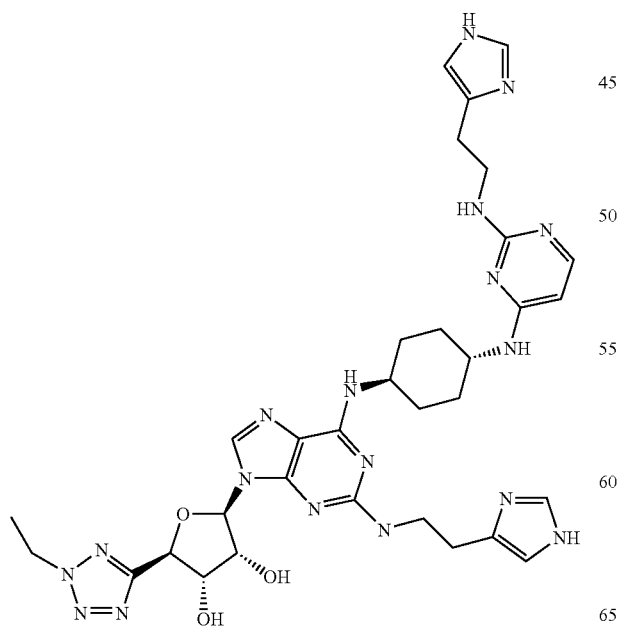

A mixture of (2R,3R,4R,5R)-2-[2-chloro-6-({trans-4-[(2-chloro-4-pyrimidinyl)amino]cyclohexyl}amino)-9H-purin-9-yl]-5-(2-ethyl-2H-tetrazol-5-yl)tetrahydrofuran-3,4-diyl diacetate (Intermediate 3) (0.23 mmol), amine (histamine) (20 m. eq.) and N,N-diisopropylethylamine (20 m. eq.) in dimethylsulfoxide (1 ml) was heated at 125° C. overnight. The cooled reaction solution was washed with tert-butyl methyl ether (2×ca. 10 ml) and the residue was dissolved in methanol (2 ml)/water (4 ml)/formic acid (0.5 ml) and purified by preparative hplc. The appropriate fractions were combined and concentrated in vacuo and freeze-dried to give the title compound, 93 mg.

LC-MS: Rt 4.72 min, MH$^+$=727

Examples 7, 8, 9 and 10 were synthesised in an analogous manner to Example 6:

| Example | Amine | Product | Product mass | LC-MS Rt | MH+ |
|---|---|---|---|---|---|
| 7 | 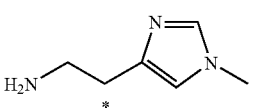 | (2R,3S,4R,5R)-2-(2-ethyl-2H-tetrazol-5-yl)-5-[2-{[2-(1-methyl-1H-imidazol-4-yl)ethyl]amino}-6-({trans-4-[(2-{[2-(1-methyl-1H-imidazol-4-yl)ethyl]amino}-4-pyrimidinyl)amino]cyclohexyl}-amino)-9H-purin-9-yl]tetrahydro-3,4-furandiol, diformate | 84 mg | 4.25 min | 755 |
| 8 | 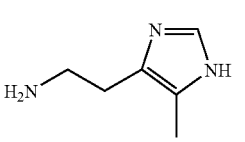 | (2R,3S,4R,5R)-2-(2-ethyl-2H-tetrazol-5-yl)-5-[2-{[2-(5-methyl-1H-imidazol-4-yl)ethyl]amino}-6-({trans-4-[(2-{[2-(5-methyl-1H-imidazol-4-yl)ethyl]amino}-4-pyrimidinyl)amino]cyclohexyl}-amino)-9H-purin-9-yl]tetrahydro-3,4-furandiol, diformate | 84 mg | 4.40 min | 755 |
| 9 | 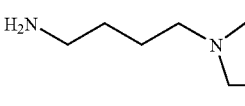 | (2R,3S,4R,5R)-2-(2-ethyl-2H-tetrazol-5-yl)-5-[2-{[4-(1-pyrrolidinyl)butyl]amino}-6-({trans-4-[(2-{[4-(1-pyrrolidinyl)butyl]amino}-4-pyrimidinyl)amino]cyclohexyl}-amino)-9H-purin-9-yl]tetrahydro-3,4-furandiol, tetraformate | 69 mg | 4.43 min | 789 |
| 10 | 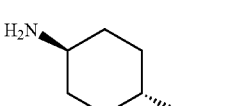 | (2R,3S,4R,5R)-2-(2-[(trans-4-aminocyclohexyl)amino]-6-{[trans-4-({2-[(trans-4-aminocyclohexyl)amino]-4-pyrimidinyl}amino)cyclohexyl]-amino}-9H-purin-9-yl)-5-(2-ethyl-2H-tetrazol-5-yl)tetrahydro-3,4-furandiol, triformate | 61 mg | 4.19 min | 733 |

*in Example 7 the amine was used as the free base which may be derived from the commercially available dihydrochloride salt.

Alternative Preparation of Example 2

Formic Acid (2R,3S,4R,5R)-2-(2-ethyl-2H-tetrazol-5-yl)-5-[2-{[2-(1-methyl-1H-imidazol-4-yl)ethyl]amino}-6-({trans-4-[(2-{[2-(1-methyl-1H-imidazol-4-yl)ethyl]amino}-1H-purin-6-yl)amino]cyclohexyl}amino)-9H-purin-9-yl]tetrahydro-3,4-furandiol (2:1)

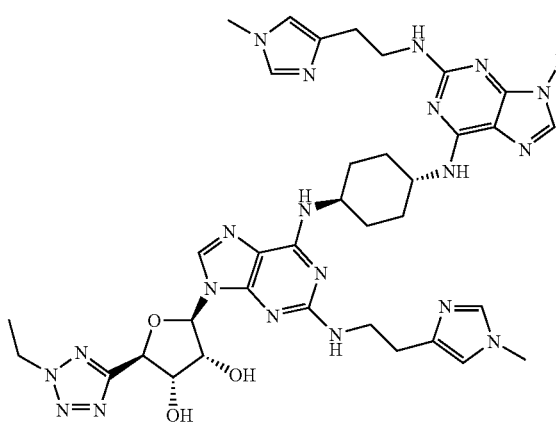

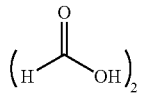

(2R,3R,4R,5R)-2-{2-Chloro-6-[(trans-4-{[2-chloro-9-(tetrahydro-2H-pyran-2-yl)-9H-purin-6-yl]amino}cyclohexyl)amino]-9H-purin-9-yl}-5-(2-ethyl-2H-tetrazol-5-yl)tetrahydrofuran-3,4-diyl diacetate (Intermediate 2) (2.85 g) was added to a solution of [2-(1-methyl-1H-imidazol-4-yl)ethyl]amine (8.2 g) and N,N-diisopropylethylamine (11.8 ml) in dimethylsulphoxide (15 ml) and heated at 125° C. under nitrogen for 20 h. The mixture was allowed to cool to room temperature and washed with diethyl ether (2×50 ml). The mixture was poured onto water (200 ml) and stirred for 30 min. The sticky solid that formed was filtered, washed with water, dissolved in methanol and evaporated down in vacuo. This was dissolved in methanol (30 ml) and 2N HCl (10 ml) added. The mixture was stirred at room temperature under nitrogen for 4 h. The methanol was removed in vacuo and the residue diluted with water (15 ml). The solution was basified with 2N aq. sodium bicarbonate solution, a solid precipitated which was filtered, washed with water and dried under vacuum to give the free base (2.19 g). A portion of the solid (1 g) was dissolved in 0.1% formic acid in water and loaded onto a C18 SPE cartridge (50 g) and washed on with 0.1% formic acid in water. The product was eluted with 10% acetonitrile/0.1% formic acid in water. The appropriate fractions were combined and the solvent removed in vacuo. The residue was then freeze-dried from water to give the title compound, 0.76 g.

LCMS; Rt 1.98 min, (MH)+ 795.

NMR (D6-DMSO+D$_2$O, 392K): 7.81δ (1H, s), 7.60δ (1H, s), 7.45δ (2H, br. s), 6.84, 6.82δ (2H, 2×s), 6.00δ (1H, d), 5.18δ (1H, d), 4.80δ (2H, m), 4.65δ (2H, q), 4.15δ (2H, m), 3.55δ (4H, t), 2.75δ (4H, 2×t), 2.10δ (4H, br. d), 1.60-1.40δ (7H, m+t).

Alternative Preparation of Example 4

Formic Acid (2R,3S,4R,5R)-2-(2-ethyl-2H-tetrazol-5-yl)-5-[2-{[4-(1-pyrrolidinyl)butyl]-amino}-6-({trans-4-[(2-{[4-(1-pyrrolidinyl)butyl]amino}-1H-purin-6-yl)amino]cyclohexyl}amino)-9H-purin-9-yl]tetrahydro-3,4-furandiol (3:1)

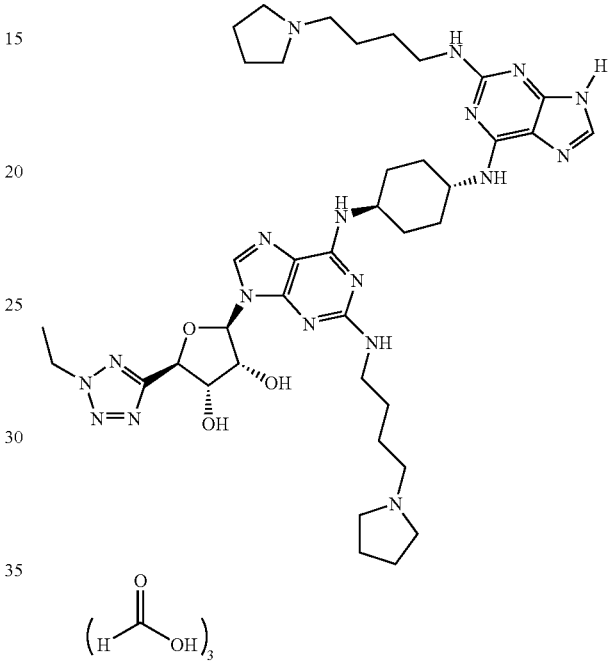

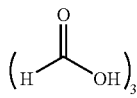

(2R,3R,4R,5R)-2-{2-Chloro-6-[(trans-4-{[2-chloro-9-(tetrahydro-2H-pyran-2-yl)-9H-purin-6-yl]amino}cyclohexyl)amino]-9H-purin-9-yl}-5-(2-ethyl-2H-tetrazol-5-yl)tetrahydrofuran-3,4-diyl diacetate (Intermediate 2) (3.0 g), [4-(1-pyrrolidinyl)butyl]amine (10.84 g) and N,N-diisopropylethylamine (13.45 ml) were stirred with dimethylsulphoxide (20 ml) at 125° C. under nitrogen for 20 h. The mixture was allowed to cool to room temperature and washed with diethyl ether (2×100 ml). The mixture was poured onto water (200 ml), stirred for 25 min and the precipitated solid was filtered, washed with water, and dried under vacuum. The solid was dissolved in methanol (30 ml) and 2N HCl added (30 ml). The mixture was heated a 60° C. for 1-2 h. The solvent was removed in vacuo and the residue partitioned between dichloromethane and 2N aq. sodium bicarbonate solution. The product went into the aqueous layer. The aqueous layer was evaporated down in vacuo and the residue triturated with methanol. The solid was filtered and the filtrate evaporated down to give a residue (5 g) which was purified by reverse phase chromatography. The solid (~4 g) was dissolved in water/formic acid solution (20 ml/0.5 ml), loaded onto a C18 SPE cartridge (70 g) and eluted with a stepped gradient of 0 to 20% acetonitrile/0.1% formic acid in water (~200 ml of each). The appropriate fractions were combined and acetonitrile removed in vacuo. The solution was then freeze-dried to give the title compound (0.769 g).

LCMS; Rt 1.98 min, (MH+)+ 829.

NMR (D6-DMSO+D$_2$O, 392K): 7.85δ (1H, s), 7.58δ (1H, s), 5.98δ (1H, d), 5.15δ (1H, d), 4.80δ (1H, t), 4.70-4.60δ (3H, m), 4.10δ (2H, br. m), 3.30δ (4H, 2×t, partially hidden by water), 3.0δ (8H, m), 2.95δ (4H, m), 2.05δ (4H, br. d), 1.85δ (8H, m), 1.75-1.30δ (15H, m+t).

Alternative Preparation of Example 7

Formic Acid (2R,3S,4R,5R)-2-(2-ethyl-2H-tetrazol-5-yl)-5-[2-{[2-(1-methyl-1H-imidazol-4-yl)ethyl]amino}-6-({trans-4-[(2-{[2-(1-methyl-1H-imidazol-4-yl)ethyl]amino}-4-pyrimidinyl)amino]cyclohexyl}amino)-9H-purin-9-yl]tetrahydro-3,4-furandiol (3:1)

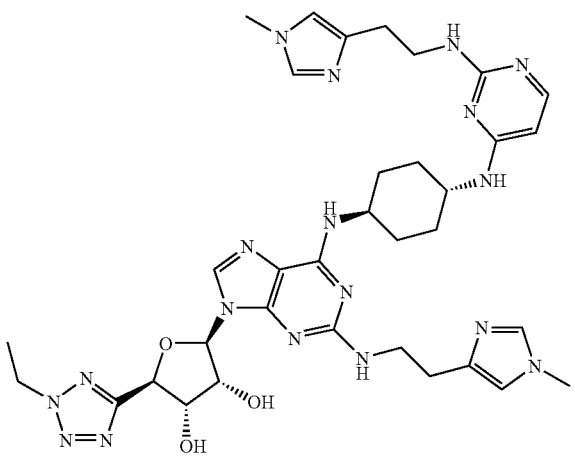

(2R,3R,4R,5R)-2-[2-Chloro-6-({trans-4-[(2-chloro-4-pyrimidinyl)amino]cyclohexyl}amino)-9H-purin-9-yl]-5-(2-ethyl-2H-tetrazol-5-yl)tetrahydrofuran-3,4-diyl diacetate (Intermediate 3) (1.53 g), [2-(1-methyl-1H-imidazol-4-yl)ethyl]amine (5.7 g) and N,N-diisopropylethylamine (8 ml) were stirred with dimethylsulphoxide (10 ml) at 125° C. under nitrogen for 18 h. The mixture was allowed to cool to room temperature and washed with tert-butyl methyl ether (2×100 ml). The mixture was diluted with water, a sticky solid precipitated which was trituated and the water decanted. The sticky solid/gum was dissolved in methanol and evaporated down in vacuo. The residue was split into two batches and purified by reverse phase chromatography using the Companion XL. Each solid was dissolved in water/acetonitrile/formic acid solution (2.5 ml/0.5 ml/0.3 ml), loaded onto a reverse phase cartridge (330 g) and eluted with a gradient of 5 to 50% acetonitrile/0.1% formic acid in water over 8 column volumes. The appropriate fractions from both runs were combined and evaporated down in vacuo. The residue was taken up in water and freeze-dried to give the title compound (1.08 g).

LCMS; Rt 1.99 min, ([M+2H]/2)$^{2+}$ 378.

NMR (D6-DMSO+D$_2$O, 392K): 7.80δ (1H, s), 7.58δ (1H, d), 7.40δ (1H, s), 6.78δ (2H, 2×s), 5.95δ (1H, d), 5.80δ (1H, d), 5.15δ (1H, d), 4.78δ (2H, m), 4.60δ (2H, q), 4.05δ (1H, m), 3.70δ (1H, m), 3.50δ (6H, s), 3.45δ (4H, 2×t), 2.70δ (4H, 2×t), 2.00δ (4H, m), 1.45δ (3H, t), 1.40δ (4H, m).

Biological Examples

Biological Activity of Compounds May be Assessed Using the Following Assays or Similar Assays Biological Example 1

In Vitro Agonist Activity Against Human Adenosine $A_1$, $A_{2A}$, $A_{2B}$ Receptors The agonist potency and selectivity of compounds against human adenosine receptors is determined using Chinese hamster ovary (CHO) cells transfected with the gene for the relevant receptor. These cells are used to measure the production of cAMP in response to compound stimulation.

The DiscoveRx assay is an enzyme complementation assay based on CHO cells that involves two fragments of β-galactosidase, enzyme acceptor (EA) and enzyme donor (ED). Following the production of cAMP EA binds to ED, active enzyme is produced and a luminescent product is formed following the addition of substrate. For both methods the effect of test compounds is determined by their effects on basal levels of cAMP ($A_{2A}$ and $A_{2B}$) or on forskolin enhanced cAMP ($A_1$).

In all of the in vitro assays the activity of test compounds is expressed as a ratio to that of the non-selective adenosine receptor agonist, N-ethyl carboxamide adenosine (NECA).

In certain embodiments of the invention compounds demonstrating activity at the $A2_A$ receptor of at least two times that of NECA may be preferred. On testing, the compounds of Examples 1-9 were found to meet this criteria.

In other embodiments of the invention compounds demonstrating greater than 100-fold selectivity for the $A2_A$ receptor over the A1 receptor may be preferred. On testing, the compounds of Examples 1-9 were found to meet this criteria.

In further embodiments of the invention compounds demonstrating greater than 100-fold selectivity for the $A2_A$ receptor over the $A2_B$ receptor may be preferred. On testing, the compounds of Examples 4 and 6-9 were found to meet this criteria.

An alternative assay system was also used for Examples 2, 4 & 7, where as in DiscoveRx, the agonist potency and selectivity of compounds against human adenosine receptors is determined using Chinese hamster ovary (CHO) cells transfected with the gene for the relevant receptor. These cells are used to measure the production of cAMP in response to compound stimulation.

A cAMP tracer is formed by the interaction between Biotin-cAMP and Streptavidin labelled with Europium-W8044 Chelate. This tracer then competes with cellular cAMP for binding to cAMP specific antibodies labelled with the dye Alexa Fluor 647.

Light pulses at 340 nm excite the Europium Chelate molecules of the cAMP tracer and, if the tracer is bound to the antibody, the energy emitted by the Eu-chelate is transferred to the Alexa Fluor molecule on the antibody. This results in an emission of light from the Alexa molecule at 665 nm which is measured.

Therefore the greater the levels of cellular cAMP produced by receptor stimulation, the less cAMP tracer can bind to the antibodies and the less energy transfer is observed, hence the fluorescent signal will be decreased.

For $G_S$-coupled receptors such as the Adenosine A2a and A2b receptors, agonist stimulation results in an increase in cAMP levels and hence a decrease in fluorescence at 665 nm. Antagonist addition will have the reverse effect.

For $G_i$-coupled receptors such as the Adenosine A1 receptor, agonist addition inhibits forskolin induced cAMP production and hence leads to an increase in fluorescence at 665 nm. Antagonism blocks the effect of the agonist and hence increases cellular cAMP and decreases the fluorescent signal.

In certain embodiments of the invention compounds demonstrating activity at the $A2_A$ receptor of at least two times that of NECA may be preferred. On testing, the compounds of Examples 2, 4 and 7 were found to meet this criteria.

In other embodiments of the invention compounds demonstrating greater than 100-fold selectivity for the $A2_A$ receptor over the A1 receptor may be preferred. On testing, the compounds of Examples 2, 4 and 7 were found to meet this criteria.

In further embodiments of the invention compounds demonstrating greater than 100-fold selectivity for the $A2_A$ receptor over the $A2_B$ receptor may be preferred. On testing, the compounds of Examples 2, 4 and 7 were found to meet this criteria.

Biological Example 2

Human Serum Albumin (HSA) Binding

Instrument: Agilent HP1100 HPLC instruments were used throughout.

HPLC columns: Chromtech Immobilised HSA HPLC column 50×3 mm was purchased from Chromtech (Cheshire, UK).

Mobile phase and detection: The mobile phase A was 50 mM pH 7.4 ammonium acetate solution, while mobile phase B was 2-Propanol (HPLC grade, Runcorn, UK). The mobile phase flow rate was 1.8 ml/min. The column temperature was kept at 30° C. The gradient profile and run time were the same with each column, the linear gradient from 0 to 30% 2-propanol was applied from 0 to 3 minutes. From 3 to 5 minutes, the mobile phase composition was constant 30% 2-propanol and 70% 50-mM ammonium acetate. From 5 min to 5.2 min the mobile phase composition was change to 100% ammonium acetate buffer only and remained the same until the end of the run. Each separation was stopped after 6 minutes. The column temperature was kept at 30° C.

Detection: Chromatograms were recorded at 230 and 254 nm by a diode array UV absorption detector at room temperature.

Calibration of the protein columns: The column performance check and the calibration have been performed before the analysis of every 96 well plate. The compounds used for the column calibrations were dissolved separately in 0.5 mg/ml concentration in 50% 2-propanol and 50% pH 7.4 ammonium acetate solution mixtures. The calibration set of compounds their literature % plasma protein binding and its linear conversion value (log K lit), as well as typical retention times, their logarithmic values, log K derived from the calibration curve and % binding data are listed in Table 1.

The literature % PPB (bound in plasma) values were converted to the linear free energy related log K values (logarithm of apparent affinity constant) using the following equation.

$$\mathrm{Log}\, K = \log\left[\frac{\%\,PPB}{(101 - \%\,PPB)}\right] - [\text{Plasma Protein}]$$

In one embodiment of the invention compounds demonstrating HSA binding greater than 90% may be preferred. The compounds of Examples 1-10 were found to meet this criteria on testing.

Biological Example 3

Inhibition of Neutrophilia

Rats are lightly anaesthetized (isofluorane in oxygen) and vehicle or test substance administered intratracheally using a cannula placed trans-orally (200 μl). Following intratracheal administration, rats are returned to their cages and allowed free access to both food and water. Thirty min later, rats are placed in a perspex box and exposed to aerosolized lipopolysaccharide (LPS) (0.15 mg/ml, serotype 0127:B8) for 15 min (Devilbiss nebuliser) at a flow rate of 15 ml/min. Animals are killed 4 h later with pentobarbital (250 mg/kg i.p.). The lungs are lavaged using 3 aliquots (5 ml) of phosphate-buffered saline (Sigma catalogue no. P3813, pH 7.4) containing heparin (10 units/ml); recovered cells are pooled (pooled volume of recovered fluid will be recorded) and centrifuged (1300 rpm for 7 min). The supernatant is removed by aspiration and the cell pellet resuspended in 1 ml phosphate-buffered saline. Total cells are counted (Sysmex Microcell Counter F-500, TOA Medical Electronics Ltd., Japan). Smears are made by diluting recovered fluid (to approximately $10^6$ cells/ml) and spinning an aliquot (100 μl) in a centrifuge (Cytospin, Shandon, UK). Smears are air dried, fixed using a solution of methanol for 10 s and stained with buffered eosin (10 s) and methylene blue/Azur 1 (5 s) (Speedy-Diff, ClinTech Ltd, Essex, UK) in order to differentiate eosinophils, neutrophils, macrophages and lymphocytes. A total of 300 cells per smear are counted by light microscopy under oil immersion (×1000).

In one embodiment of the invention compounds demonstrating inhibition of neutrophilia of (>50%) may be preferred. On testing at a concentration of 100 ug/kg, the compounds of Examples 1, 2, 3, 4, 6 and 7 were found to meet this criteria. The compounds of Examples 5, 8, 9 and 10 were not tested.

Examples 2, 4 and 7 were retested at 30 ug/kg using a method similar to that described above. Of these 3 compounds only Example 4 gave >50% inhibition.

Biological Example 4

In Vitro Agonist Activity Against Human Adenosine $A_3$ Receptors

The adenosine $A_3$ agonist potency of compounds are determined using Chinese Hamster ovary cells stably expressing the human adenosine $A_3$ receptor and the cAMP response element SPAP (secreted placental alkaline phosphatase). Increasing the level of cAMP in theses cell causes an increase in the transcription of the SPAP reporter gene, which can be quantified by addition of a colour substrate to measure a coloured product. The adenosine $A_3$ receptor is Gi linked so levels cAMP have to be enhanced by forskolin in these cells. Activation of the adenosine $A_3$ receptor is determined by the reduction of forskolin enhanced cAMP, which is measured as a decrease in the coloured product. The Adenosine $A_3$ activity

TABLE 1

Calibration set of compounds with their literature and typical measured chromatographic data obtained with the HSA column. (Literature data were obtained from ref. Valko K, Nunhuck S, Bevan C, Abraham M C, Reynolds D P, (2003) J. Pharm. Sci. 92 p2236-2248.

| Compound | Literature % PPB | tR | logtR | lit logK | logK measured | % HSA measured |
|---|---|---|---|---|---|---|
| Warfarin2 | 98 | 3.42 | 0.53 | 1.51 | 1.433 | 97.4 |
| Nizatidine | 35 | 0.40 | -0.0.39 | -0.28 | -0.49 | 24.6 |
| Bromazepam | 60 | 1.16 | 0.06 | 0.17 | 0.45 | 74.7 |
| Carbamazepine | 75 | 1.35 | 0.13 | 0.46 | 0.59 | 80.5 |
| Budesonide | 88 | 1.6 | 0.20 | 0.83 | 0.75 | 85.6 |
| Piroxicam | 94.5 | 3.1 | 0.49 | 1.16 | 1.34 | 96.6 |
| Nicardipine | 95 | 2.7 | 0.43 | 1.20 | 1.22 | 95.0 |
| Ketoprofen | 98.7 | 3.8 | 0.58 | 1.63 | 1.53 | 9.1 |
| Indomethacin | 99 | 4.5 | 0.66 | 1.69 | 1.69 | 98.9 |
| Diclofenac | 99.8 | 5.0 | 0.70 | 1.92 | 1.78 | 99.3 | of the test compounds is expressed as a ratio to that of the non-selective adenosine receptor agonist, N-ethyl carboxamide adenosine (NECA).

Examples 2, 8, 9, and 10 were functionally inactive over the concentration range of the assay. Examples 1, 3, 6 and 7 were greater than 100-fold selective over $A_{2A}$. Examples 4 and 5 were greater than 10-fold selective over $A_{2A}$.

All publications, including but not limited to patents and patent applications, cited in this specification are herein incorporated by reference as if each individual publication were specifically and individually indicated to be incorporated by reference herein as though fully set forth.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

What is claimed is:

1. A compound of formula (I):

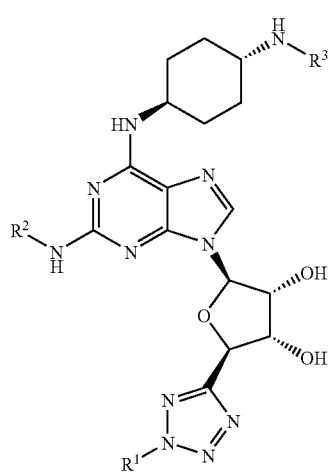

(I)

wherein:

$R^1$ represents methyl or ethyl;

$R^2$ represents a substituent moiety selected from the group consisting of:

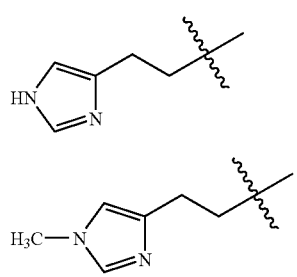

(i)

(ii)

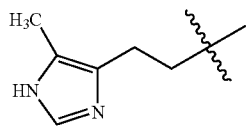

(iii)

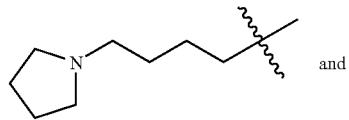

(iv)

and

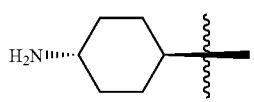

(v)

$R^3$ represents a substituent moiety selected from the group consisting of:

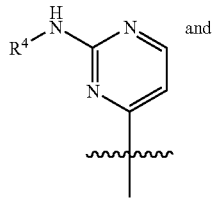

(a)

and

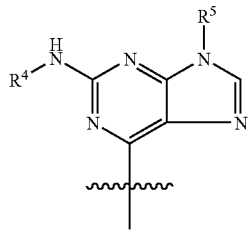

(b)

wherein $R^4$ represents a substituent moiety selected from the group consisting of:

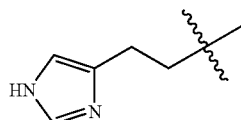

(i)

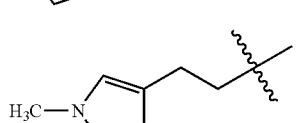

(ii)

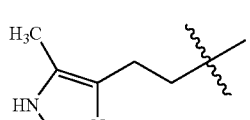

(iii)

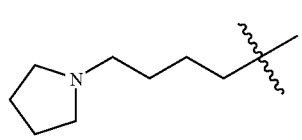

(iv)

-continued

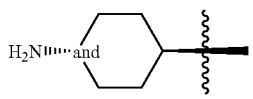

(v)

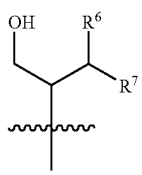

(vi)

R⁵ represents a substituent moiety selected from the group consisting of hydrogen, $C_{1-4}$-alkyl, $C_{1-4}$alkylaryl, $C_{1-4}$alkylheteroaryl and $C_{1-4}$hydroxyalkyl;

R⁶ and R⁷ are independently selected from the group consisting of hydrogen, methyl, phenyl and a salt thereof.

2. A compound according to claim 1, wherein R¹ represents ethyl.

3. A compound according to claim 1, wherein R² represents group (i), (ii), (iii) or (iv).

4. A compound according to claim 3, wherein R² represents group (ii).

5. A compound according to claim 3, wherein R² represents group (iv).

6. A compound according to claim 1, wherein R³ represents group (a).

7. A compound according to claim 1, wherein R³ represents group (b).

8. A compound according to claim 1, wherein R⁵ represents H.

9. A compound according to claim 1, wherein R⁴ represents group (i), (ii), (iii), (iv) or (v).

10. A compound according to claim 9, wherein R⁴ represents group (ii).

11. A compound according to claim 9, wherein R⁴ represents group (iv).

12. A compound which is:
(2R,3S,4R,5R)-2-(2-ethyl-2H-tetrazol-5-yl)-5-[2-{[2-(1H-imidazol-4-yl)ethyl]amino}-6-({trans-4-[(2-{[2-(1H-imidazol-4-yl)ethyl]amino}-1H-purin-6-yl)amino]cyclohexyl}amino)-9H-purin-9-yl]tetrahydro-3,4-furandiol;
(2R,3S,4R,5R)-2-(2-ethyl-2H-tetrazol-5-yl)-5-[2-{[2-(1-methyl-1H-imidazol-4-yl)ethyl]amino}-6-({trans-4-[(2-{[2-(1-methyl-1H-imidazol-4-yl)ethyl]amino}-1H-purin-6-yl)amino]cyclohexyl}amino)-9H-purin-9-yl]tetrahydro-3,4-furandiol;
(2R,3S,4R,5R)-2-(2-ethyl-2H-tetrazol-5-yl)-5-[2-{[2-(5-methyl-1H-imidazol-4-yl)ethyl]amino}-6-({trans-4-[(2-{[2-(5-methyl-1H-imidazol-4-yl)ethyl]amino}-1H-purin-6-yl)amino]cyclohexyl}amino)-9H-purin-9-yl]tetrahydro-3,4-furandiol;
(2R,3S,4R,5R)-2-(2-ethyl-2H-tetrazol-5-yl)-5-[2-{[4-(1-pyrrolidinyl)butyl]amino}-6-({trans-4-[(2-{[4-(1-pyrrolidinyl)butyl]amino}-1H-purin-6-yl)amino]cyclohexyl}amino)-9H-purin-9-yl]tetrahydro-3,4-furandiol;
(2R,3R,4S,5R)-2-(2-[(trans-4-aminocyclohexyl)amino]-6-{[trans-4-({2-[(trans-4-aminocyclohexyl)amino]-9H-purin-6-yl}amino)cyclohexyl]amino}-9H-purin-9-yl)-5-(2-ethyl-2H-tetrazol-5-yl)tetrahydro-3,4-furandiol;
(2R,3S,4R,5R)-2-(2-ethyl-2H-tetrazol-5-yl)-5-[2-{[2-(1H-imidazol-4-yl)ethyl]amino}-6-({trans-4-[(2-{[2-(1H-imidazol-4-yl)ethyl]amino}-4-pyrimidinyl)amino]cyclohexyl}amino)-9H-purin-9-yl]tetrahydro-3,4-furandiol;
(2R,3S,4R,5R)-2-(2-ethyl-2H-tetrazol-5-yl)-5-[2-{[2-(1-methyl-1H-imidazol-4-yl)ethyl]amino}-6-({trans-4-[(2-{[2-(1-methyl-1H-imidazol-4-yl)ethyl]amino}-4-pyrimidinyl)amino]cyclohexyl}amino)-9H-purin-9-yl]tetrahydro-3,4-furandiol;
(2R,3S,4R,5R)-2-(2-ethyl-2H-tetrazol-5-yl)-5-[2-{[2-(5-methyl-1H-imidazol-4-yl)ethyl]amino}-6-({trans-4-[(2-{[2-(5-methyl-1H-imidazol-4-yl)ethyl]amino}-4-pyrimidinyl)amino]cyclohexyl}amino)-9H-purin-9-yl]tetrahydro-3,4-furandiol;
(2R,3S,4R,5R)-2-(2-ethyl-2H-tetrazol-5-yl)-542-{[4-(1-pyrrolidinyl)butyl]amino}-6-({trans-4-[(2-{[4-(1-pyrrolidinyl)butyl]amino}-4-pyrimidinyl)amino]cyclohexyl}amino)-9H-purin-9-yl]tetrahydro-3,4-furandiol; or
(2R,3R,4S,5R)-2-(2-[(trans-4-aminocyclohexyl)amino]-6-{[trans-4-({2-[(trans-4-aminocyclohexyl)amino]-4-pyrimidinyl}amino)cyclohexyl]amino}-9H-purin-9-yl)-5-(2-ethyl-2H-tetrazol-5-yl)tetrahydro-3,4-furandiol;
or a salt of any one thereof.

13. A compound of formula (I) which is:
(2R,3S,4R,5R)-2-(2-ethyl-2H-tetrazol-5-yl)-5-[2-{[2-(1-methyl-1H-imidazol-4-yl)ethyl]amino}-6-({trans-4-[(2-{[2-(1-methyl-1H-imidazol-4-yl)ethyl]amino}-1H-purin-6-yl)amino]cyclohexyl}amino)-9H-purin-9-yl]tetrahydro-3,4-furandiol;
(2R,3S,4R,5R)-2-(2-ethyl-2H-tetrazol-5-yl)-542-{[4-(1-pyrrolidinyl)butyl]amino}-6-({trans-4-[(2-{[4-(1-pyrrolidinyl)butyl]amino}-1H-purin-6-yl)amino]cyclohexyl}amino)-9H-purin-9-yl]tetrahydro-3,4-furandiol; or
(2R,3S,4R,5R)-2-(2-ethyl-2H-tetrazol-5-yl)-5-[2-{[2-(1-methyl-1H-imidazol-4-yl)ethyl]amino}-6-({trans-4-[(2-{[2-(1-methyl-1H-imidazol-4-yl)ethyl]amino}-4-pyrimidinyl)amino]cyclohexyl}amino)-9H-purin-9-yl]tetrahydro-3,4-furandiol;
or a salt or solvate of any one thereof.

14. A pharmaceutical composition comprising a compound of formula (I) according to claim 1, and one or more pharmaceutically acceptable diluents or carriers.

15. A method of treatment of inflammatory diseases which comprises administering to a patient an effective amount of a compound according to claim 1.

* * * * *